(12) United States Patent
Kishida et al.

(10) Patent No.: US 9,957,285 B2
(45) Date of Patent: *May 1, 2018

(54) METAL COMPLEX, ADSORBENT, SEPARATING MATERIAL, AND 1, 3-BUTADIENE SEPARATION METHOD

(71) Applicant: SHOWA DENKO K.K., Tokyo (JP)

(72) Inventors: Keisuke Kishida, Oita (JP); Yoshihiro Watanabe, Oita (JP); Yoshikuni Okumura, Oita (JP)

(73) Assignee: SHOWA DENKO K.K., Tokyo (JP)

( * ) Notice: Subject to any disclaimer, the term of this patent is extended or adjusted under 35 U.S.C. 154(b) by 131 days.

This patent is subject to a terminal disclaimer.

(21) Appl. No.: 14/906,908

(22) PCT Filed: Jul. 1, 2014

(86) PCT No.: PCT/JP2014/067518
§ 371 (c)(1),
(2) Date: Jan. 22, 2016

(87) PCT Pub. No.: WO2015/012067
PCT Pub. Date: Jan. 29, 2015

(65) Prior Publication Data
US 2016/0159823 A1    Jun. 9, 2016

(30) Foreign Application Priority Data
Jul. 26, 2013  (JP) ................................. 2013-155591

(51) Int. Cl.
*B01D 53/02*  (2006.01)
*B01D 53/22*  (2006.01)
(Continued)

(52) U.S. Cl.
CPC ................ *C07F 3/06* (2013.01); *B01D 53/02* (2013.01); *B01D 53/228* (2013.01); *B01D 69/14* (2013.01);
(Continued)

(58) Field of Classification Search
CPC .. B01D 53/02; B01D 53/0462; B01D 53/047; B01D 53/22; B01D 53/228; B01D 69/10;
(Continued)

(56) References Cited

U.S. PATENT DOCUMENTS

| 3,992,471 A | 11/1976 | Priegnitz | |
| 2008/0214806 A1* | 9/2008 | Schubert | ................ B01D 53/02 544/226 |
| 2014/0190436 A1* | 7/2014 | Inubushi | ................ B01D 53/02 123/1 A |

FOREIGN PATENT DOCUMENTS

| JP | 51-043702 A | 4/1976 |
| JP | 2010-180201 A | 8/2010 |

(Continued)

OTHER PUBLICATIONS

JP2012180322A English Translation, AIPN, obtained Jul. 25, 2017.*

(Continued)

*Primary Examiner* — Jason M Greene
(74) *Attorney, Agent, or Firm* — Sughrue Mion, PLLC

(57) ABSTRACT

A separating material superior to conventional separating materials, and a separation method are provided, with which 1,3-butadiene is selectively separated and recovered from a mixed gas including 1,3-butadiene and C4 hydrocarbons other than 1,3-butadiene. A metal complex, which comprises a dicarboxylic acid compound (I) (see (I) below) represented by general formula (I), an ion of a metal such as beryllium, and a dipyridyl compound (II) represented by general for- (Continued)

mula (II), namely L-Z-L (II) (see L below), is characterized by including, as the dipyridyl compound (II), at least two different dipyridyl compounds (II). The metal complex is used as a 1,3-butadiene separating material. Formula (I) L is represented by any of the compounds below.

16 Claims, 7 Drawing Sheets

(51) Int. Cl.
B01D 69/14 (2006.01)
C07F 3/06 (2006.01)
B01J 20/22 (2006.01)
B01J 20/28 (2006.01)
C07C 7/12 (2006.01)
C07C 201/12 (2006.01)
C07D 213/06 (2006.01)
C07D 213/68 (2006.01)
C07D 213/70 (2006.01)
B01J 20/34 (2006.01)
B01D 53/04 (2006.01)
B01D 53/047 (2006.01)

(52) U.S. Cl.
CPC ........ B01J 20/226 (2013.01); B01J 20/28035 (2013.01); B01J 20/3483 (2013.01); C07C 7/12 (2013.01); C07C 201/12 (2013.01); C07D 213/06 (2013.01); C07D 213/68 (2013.01); C07D 213/70 (2013.01); *B01D 53/047* (2013.01); *B01D 53/0462* (2013.01); *B01D 2253/112* (2013.01); *B01D 2253/20* (2013.01); *B01D 2256/24* (2013.01); *B01D 2257/7022* (2013.01); *B01D 2325/12* (2013.01); *Y02C 10/08* (2013.01)

(58) Field of Classification Search
CPC .... B01D 69/142; B01D 69/147; B01D 71/00; B01D 71/06; B01D 2253/20; B01D 2253/204; B01D 2256/24; B01D 2257/702; B01D 2325/12; C07C 7/12; B01J 20/223; B01J 20/226; B01J 20/28033; B01J 20/3425; B01J 20/3491; C07D 213/06; C07D 213/068; C07D 213/07; C07F 3/06
See application file for complete search history.

(56) References Cited

FOREIGN PATENT DOCUMENTS

| JP | 2011-051949 A | 3/2011 |
| JP | 2011-068631 A | 4/2011 |
| JP | 2012-031161 A | 2/2012 |
| JP | 2012-180322 A | 9/2012 |
| JP | 2012180322 A * | 9/2012 |
| JP | 2012-193122 A | 10/2012 |
| JP | 2013-216622 A | 10/2013 |
| WO | 2013/024761 A1 | 2/2013 |

OTHER PUBLICATIONS

Kazuhiro Uemura, et al., Future Materials, 2002, pp. 44-51, vol. 2.
Ryotaro Matsuda, et al., Petrotech, 2003, pp. 97-104, vol. 26.
Satoshi Horike, et al., "Dense Coordination Network Capable of Selective $CO_2$ Capture from C1 and C2 Hydrocarbons", Journal of American Chemical Society, 2012, pp. 9852-9855, vol. 134.
Lu-Fang Ma, et al., "Significant Positional Isomeric Effect on Structural Assemblies of Zn(II) and Cd (II) Coordination Polymers Based on Bromoisophthalic Acids and Various Dipyridyl-Type Coligands", Crystal Growth and Design, 2011, pp. 175-184, vol. 11.
Susan A. Bourne, et al., "Coexisting covalent and noncovalent nets: parallel interpenetration of a puckered rectangular coordination polymer and aromatic noncovalent nets", Chemical Communications, 2001, pp. 861-862.
Lu-Fang Ma, et al., "Syntheses, Structures, and Photoluminescence of a Series of $d^{10}$ Coordination Polymers with R-Isophthalate (R=-OH,-$CH_3$, and -$C(CH_3)_3$)", Crystal Growth & Design, 2009, pp. 5334-5342, vol. 9.
Satoshi Horike, et al., "A solid solution approach to 2D coordination polymers for $CH_4$/$CO_2$ and $CH_4$/$C_2H_6$ gas separation: equilibrium and kinetic studies", Chemical Science, 2012, pp. 116-120, vol. 3.
International Search Report for PCT/JP2014/067518 dated Sep. 9, 2014 [PCT/ISA/210].

* cited by examiner

METAL COMPLEX, ADSORBENT, SEPARATING MATERIAL, AND 1,3-BUTADIENE SEPARATION METHOD

CROSS REFERENCE TO RELATED APPLICATIONS

This application is a National Stage of International Application No. PCT/JP2014/067518 filed Jul. 1, 2014 (claiming priority based on Japanese Patent Application No. 2013-155591 filed Jul. 26, 2013), the contents of which are incorporated herein by reference in their entirety.

TECHNICAL FIELD

The present invention relates to a metal complex, an adsorbent and separating material composed thereof, and a 1,3-butadiene separation method.

BACKGROUND ART

Various adsorbents have been previously developed for use in fields including deodorization or exhaust gas treatment. Active charcoal is a typical example thereof. Active charcoal has been widely used in various industries in applications including air purification, desulfurization, denitrification or removal of harmful substances by utilizing its superior adsorption performance. More recently, due to the growing demand for nitrogen gas for use in applications including semiconductor production processes, a method for producing nitrogen is thus used that comprises producing nitrogen from air by pressure swing adsorption or temperature swing adsorption using molecule sieve carbon. In addition, molecular sieve carbon is also applied to the purification and separation of various gases, such as the purification of hydrogen from methanol cracking gas.

When separating a mixed gas by pressure swing adsorption or temperature swing adsorption, molecular sieve carbon or zeolite and the like is typically used as a separating adsorbent, and separation is carried out by the differences in its equilibrium adsorption amounts and/or adsorption rates. However, in the case of separating a mixed gas by the difference in equilibrium adsorption amounts, since the conventional adsorbents are unable to selectively adsorb only a gas that is desired to be removed, the separation factor is smaller, making increased size of the apparatus unavoidable. In addition, in the case of separating a mixed gas by the difference in adsorption rates, although only a gas desired to be removed can be adsorbed depending on the type of gas, since it is necessary to alternate between adsorption and desorption, the apparatus inevitably becomes large in this case as well.

1,3-butadiene is an example of a hydrocarbon gas that is targeted for separation and recovery. 1,3-butadiene is a compound that is useful as a starting material for the production of synthetic rubber as well as an intermediate of an extremely large number of compounds. 1,3-butadiene is typically produced by thermal decomposition of naphtha or dehydrogenation of butene. In these production methods, 1,3-butadiene is obtained in the form of one component of a mixed gas. Thus, it is necessary to selectively separate and recover 1,3-butadiene from this mixed gas. Examples of main components in the mixed gas having four carbon atoms include 1,3-butadiene, isobutene, 1-butene, trans-2-butene, cis-2-butene, n-butane and isobutane. Since these compounds have the same number of carbon atoms and similar boiling points, they are difficult to separate from each other using industrial distillation methods.

Another example of a separation method is extractive distillation. Since this method is an absorption method that uses a polar solvent, such as DMF, an extremely large amount of energy is required when recovering 1,3-butadiene from the polar solvent. Thus, an adsorption method to separate and recover 1,3-butadiene using less energy is desired.

However, since conventional porous materials (Patent Document 1) exhibit low separation performance with respect to the target gas, multi-step separation is required, thereby leading to unavoidable increases in size of the separation apparatus.

Porous metal complexes that induce a dynamic structural change by an external stimulus have been developed as adsorbents that provide separation performance superior to that of conventional porous materials (Non-Patent Document 1 and Non-Patent Document 2). In the case of using the porous materials described in these publications as gas adsorbents, a unique phenomenon has been observed in which, although gas is not adsorbed below a certain pressure, gas begins to be adsorbed once that pressure is exceeded. In addition, a phenomenon has been observed in which the gate-opening pressure varies depending on the type of gas.

In the case of applying this porous material to an adsorbent in a pressure swing adsorption system, gas can be separated extremely efficiently. In addition, the range of pressure swing can be narrowed, thereby contributing to energy savings. Moreover, this can contribute to downsize and cost-reduction of the gas separation apparatus, enabling to enhance cost competitiveness for both high-purity gas products and finished products made from the high-purity gases.

However, to meet growing demands for even greater cost reductions, it is necessary to further improve adsorption and separation performance.

A metal complex [Zn(R-ip)(L)] (wherein R represents H, $CH_3$, $NO_2$, Br or I, and L represents 1,2-di(4-pyridyl)ethylene, 1,2-di(4-pyridyl)ethane or 4,4'-azopyridine) has been disclosed and the complex is composed of various types of isophthalic acid derivatives, zinc ion and a dipyridyl compound capable of bidentate coordination with a metal ion (Patent Document 2 and Non-Patent Documents 3 to 6). However, these disclosures do not mention the effect of mixing two or more types of bidentate dipyridyl compounds on adsorption and separation performance.

Metal complexes composed of a zinc ion, various types of isophthalic acid derivatives and 4,4'-bipyridyl have been disclosed during the course of studies about the impact of mixing ligands on gate-opening pressure (Patent Document 3 and Non-Patent Document 7). However, these disclosures also do not mention the effect of mixing bidentate dipyridyl compounds on adsorption and separation performance.

PRIOR ART DOCUMENTS

Patent Documents

[Patent Document 1] Japanese Unexamined Patent Publication No. S51-43702
[Patent Document 2] Japanese Unexamined Patent Publication No. 2012-031161

[Patent Document 3] Japanese Unexamined Patent Publication No. 2011-068631

Non-Patent Documents

[Non-Patent Document 1] Kazuhiro Uemura and Susumu Kitagawa, Future Materials, Vol. 2, pp. 44-51 (2002)

[Non-Patent Document 2] Ryotaro Matsuda and Susumu Kitagawa, Petrotech, Vol. 26, pp. 97-104 (2003)

[Non-Patent Document 3] Satoshi Horike, Keisuke Kishida, Yoshihiro Watanabe, Yasutaka Inubushi, Daiki Umeyama, Masayuki Sugimoto, Tomohiro Fukushima, Munehiro Inukai and Susumu Kitagawa, Journal of American Chemical Society, Vol. 134, pp. 9852-9855 (2012)

[Non-Patent Document 4] Lu-Fang Ma, Xiu-Qin Li, Qing-Lei Meng, Li-Ya Wang, Miao Du and Hong-Wei Hou, Crystal Growth and Design, Vol. 11, pp. 175-184 (2011)

[Non-Patent Document 5] Susan A. Bourne, Jianjiang Lu, Brian Moulton and Michael J. Zaworotko, Chemical Communications, pp. 861-862 (2001)

[Non-Patent Document 6] Lu-Fang Ma, Li-Ya Wang, Jiang-Liang Hu, Yao-Yu Wang and Guo-Ping Yang, Crystal Growth and Design, Vol. 9, pp. 5334-5342 (2009)

[Non-Patent Document 7] Satoshi Horike, Yasutaka Inubushi, Takashi Hori, Tomohiro Fukushima and Susumu Kitagawa, Chemical Science, Vol. 3, pp. 116-120 (2012)

SUMMARY OF THE INVENTION

Problems to be Solved by the Invention

An object of the present invention is to provide a metal complex that can be used as a gas adsorbent having a larger effective adsorption amount than the prior art or as a gas separating material having superior mixed gas separation performance than the prior art, and more particularly, a separating material and separation method that are superior to the prior art in that they are capable of selectively separating and recovering 1,3-butadiene from a mixed gas containing 1,3-butadiene and hydrocarbons having four carbon atoms other than 1,3-butadiene (such as butanes and butenes).

Means for Solving the Problems

As a result of extensive studies, the inventors of the present invention have found that the aforementioned object can be achieved in the case of a metal complex composed of a metal ion, a dicarboxylic acid compound (I) and an organic ligand (II) capable of bidentate coordination, wherein the organic ligand (II) is composed of two or more types of a dipyridyl compound (II), thereby leading to completion of the present invention. Namely, the present invention relates to [1] to [15] indicated below.

[1] A metal complex consisting of:
a dicarboxylic acid compound (I) represented by the following general formula (I):

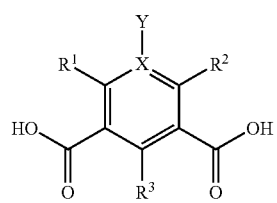

(I)

wherein X represents a carbon atom or nitrogen atom, Y represents a hydrogen atom, optionally substituted alkyl group having 1 to 4 carbon atoms, alkenyl group having 2 to 4 carbon atoms, alkoxy group having 1 to 4 carbon atoms, formyl group, acyloxy group having 2 to 4 carbon atoms, hydroxyl group, alkoxycarbonyl group having 2 to 4 carbon atoms, nitro group, cyano group, amino group, monoalkylamino group having 1 to 4 carbon atoms, dialkylamino group having 2 to 4 carbon atoms, acylamino group having 2 to 4 carbon atoms, sulfo group, sulfonate group or halogen atom in the case X represents a carbon atom or Y is not present in the case X represents a nitrogen atom, and $R^1$, $R^2$ and $R^3$ respectively and independently represent a hydrogen atom, optionally substituted alkyl group having 1 to 4 carbon atoms or halogen atom;

an ion of at least one type of metal selected from the group consisting of beryllium, magnesium, calcium, strontium, barium, titanium, vanadium, chromium, manganese, iron, ruthenium, cobalt, rhodium, nickel, palladium, platinum, copper, zinc and cadmium; and, a dipyridyl compound (II) represented by the following general formula (II):

L-Z-L  (II)

wherein L is represented by any of the following formulas:

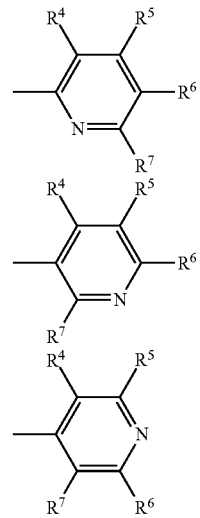

wherein $R^4$, $R^5$, $R^6$ and $R^7$ respectively and independently represent a hydrogen atom, alkyl group having 1 to 4 carbon atoms or a halogen atom, and Z represents —$CR^8R^9$—$CR^{10}R^{11}$— (wherein $R^8$, $R^9$, $R^{10}$ and $R^{11}$ respectively and independently represent a hydrogen atom, alkyl group having 1 to 4 carbon atoms, hydroxyl group or halogen atom), an alkylene group having 3 to 4 carbon atoms, —CH=CH—, —C≡C—, —S—, —N=N—, —O—CH$_2$—, —NH—CH$_2$— or —NHCO—); wherein two or more different types of the dipyridyl compound (II) are contained as the dipyridyl compound (II).

[2] The metal complex described in [1], wherein Z in the general formula (II) is —$CR^8R^9$—$CR^{10}R^{11}$— (wherein $R^8$, $R^9$, $R^{10}$ and $R^{11}$ respectively and independently represent a hydrogen atom, alkyl group having 1 to 4 carbon atoms, hydroxyl group or halogen atom), an alkylene group having 3 to 4 carbon atoms, —CH=CH—, —S— or —NHCO—.

[3] The metal complex described in [1] or [2], wherein a combination of the dipyridyl compound (II) is any of 1,2-di(4-pyridyl)ethylene and 1,2-di(4-pyridyl)ethane, 1,2-di(4-pyridyl)ethylene and 1,2-di(4-pyridyl)ethylene glycol, 1,2-di(4-pyridyl)ethylene and 4,4'-dipyridyl disulfide or 1,2-di(4-pyridyl)ethylene and 1,3-di(4-pyridyl)propane.

[4] The metal complex described in any of [1] to [3], wherein the dicarboxylic acid compound (I) is at least one selected from the group consisting of isophthalic acid, 5-methylisophthalic acid and 5-nitroisophthalic acid.

[5] The metal complex described in any of [1] to [4], wherein the metal ion is at least one selected from the group consisting of a cobalt ion, nickel ion and zinc ion.

[6] An adsorbent comprising the metal complex described in any of [1] to [5].

[7] The adsorbent described in [6], wherein the adsorbent is an adsorbent for adsorbing carbon dioxide, hydrogen gas, carbon monoxide, oxygen gas, nitrogen gas, hydrocarbons having 1 to 5 carbon atoms, rare gas, hydrogen sulfide, ammonia, sulfur oxide, nitrogen oxide, siloxane, water vapor or organic vapor.

[8] A separating material comprising the metal complex described in any of [1] to [5].

[9] The separating material described in [8], wherein the separating material selectively separates 1,3-butadiene from a mixed gas containing 1,3-butadiene and a hydrocarbon having four carbon atoms other than 1,3-butadiene.

[10] The separating material described in [9], wherein the hydrocarbon having four carbon atoms other than 1,3-butadiene is at least one selected from the group consisting of 1-butene, isobutene, trans-2-butene, cis-2-butene, isobutane and n-butane.

[11] The separating material described in [8], wherein the separating material is a separating material for separating carbon dioxide, hydrogen gas, carbon monoxide, oxygen gas, nitrogen gas, hydrocarbons having 1 to 5 carbon atoms, rare gas, hydrogen sulfide, ammonia, sulfur oxide, nitrogen oxide, siloxane, water vapor or organic vapor.

[12] A separation membrane comprising a porous support and the separating material described in any of [8] to [11] attached to the surface of the porous support.

[13] A separation membrane comprising a polymeric material and the separating material described in any of [8] to [11] kneaded and dispersed in the polymeric material.

[14] A method for producing the metal complex described in [1], comprising reacting a salt of at least one type of metal selected from the group consisting of beryllium, magnesium, calcium, strontium, barium, titanium, vanadium, chromium, manganese, iron, ruthenium, cobalt, rhodium, nickel, palladium, platinum, copper, zinc and cadmium, the dicarboxylic acid compound (I), and two or more types of the dipyridyl compound (II) and precipitating a metal complex, wherein wet grinding is carried out during the reaction.

[15] A 1,3-butadiene separation method comprising: an adsorption step for contacting a separating material with a mixed gas containing 1,3-butadiene and a hydrocarbon having four carbon atoms other than 1,3-butadiene and selectively adsorbing 1,3-butadiene onto the separating material, followed by a regeneration step for desorbing the 1,3-butadiene adsorbed onto the separating material from the separating material and capturing the released 1,3-butadiene, wherein the separating material is the separating material described in any of [8] to [10].

EFFECTS OF THE INVENTION

According to the present invention, 1,3-butadiene can be separated and recovered from a mixed gas containing 1,3-butadiene at a higher level of separation performance than that of the prior art.

The aforementioned description should not be interpreted as disclosing all embodiments of the present invention or all advantages relating to the present invention.

MODE FOR CARRYING OUT THE INVENTION

<Metal Complex>

Figure 1:
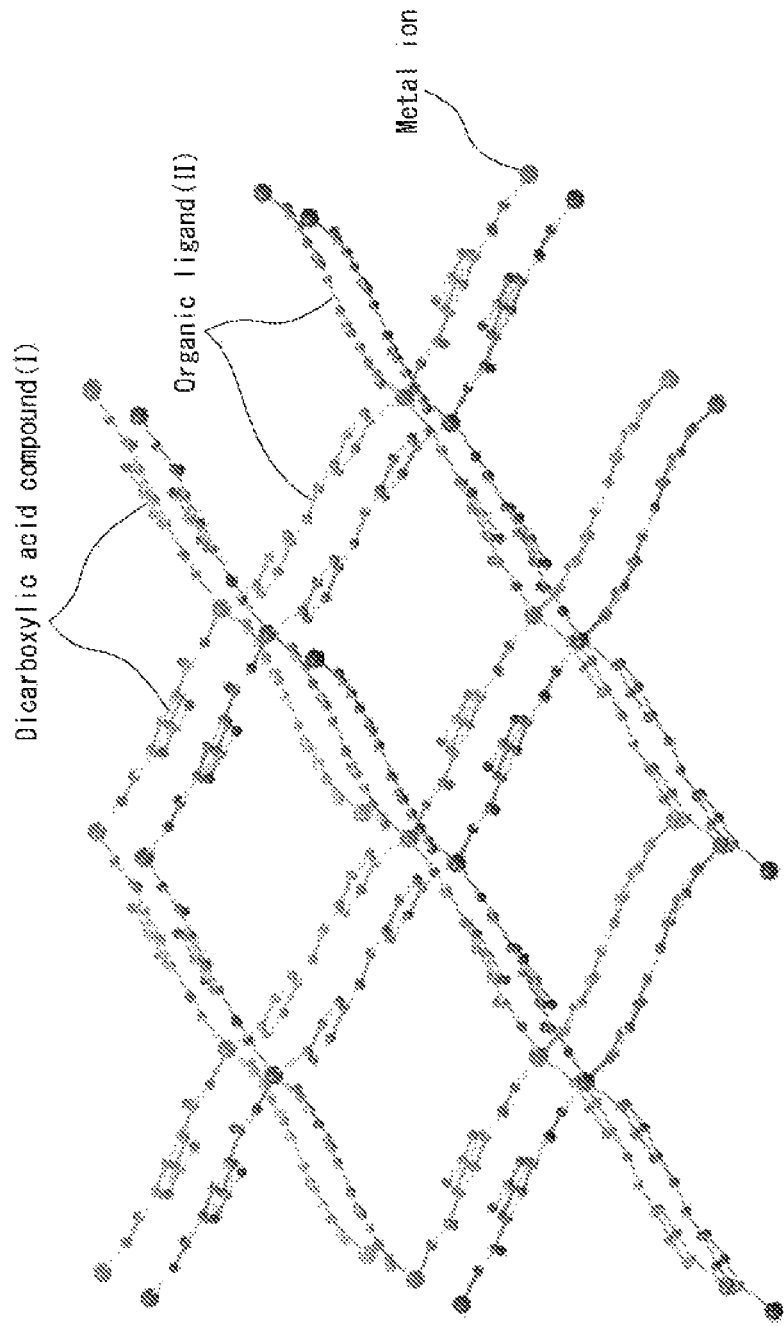
FIG. 1 is a schematic diagram showing the structure of a pseudo-diamondoid framework.

The metal complex of the present invention is composed of a dicarboxylic acid compound (I), a specific metal ion, and an organic ligand (II) capable of bidentate coordination with the metal ion, wherein organic ligand (II) comprises two or more different types of a dipyridyl compound (II).

Since the metal complex of the present invention can selectively adsorb and/or desorb a specific substance under certain conditions (pressure, temperature), it can be used as an adsorbent or separating material.

An adsorbent containing the metal complex of the present invention can be used to adsorb, for example, carbon dioxide, hydrogen gas, carbon monoxide, oxygen gas, nitrogen gas, hydrocarbons having 1 to 5 carbon atoms, rare gas, hydrogen sulfide, ammonia, sulfur oxide, nitrogen oxide, siloxane, water vapor or organic vapor.

A separating material containing the metal complex of the present invention can be used to selectively separate 1,3-butadiene from, for example, a mixed gas containing 1,3-butadiene and hydrocarbons having four carbon atoms other than 1,3-butadiene. The hydrocarbon having four carbon atoms other than 1,3-butadiene can be at least one selected from the group consisting of 1-butene, isobutene, trans-2-butene, cis-2-butene, isobutane and n-butane. In addition, a separating material containing the metal complex of the present invention can be used to separate carbon dioxide, hydrogen gas, carbon monoxide, oxygen gas, nitrogen gas, hydrocarbons having 1 to 5 carbon atoms, rare gas, hydrogen sulfide, ammonia, sulfur oxide, nitrogen oxide, siloxane, water vapor or organic vapor.

The metal complex of the present invention can be produced by reacting the dicarboxylic acid compound (I), a salt of at least one type of metal selected from the group consisting of beryllium, magnesium, calcium, strontium, barium, titanium, vanadium, chromium, manganese, iron, ruthenium, cobalt, rhodium, nickel, palladium, platinum, copper, zinc and cadmium, and two or more types of the dipyridyl compound (II), capable of bidentate coordination with the metal ion, for several minutes to several days in a solvent, and precipitating crystals.

<Dicarboxylic Acid Compound (I)>

The dicarboxylic acid compound (I) used in the present invention is represented by the following general formula (I):

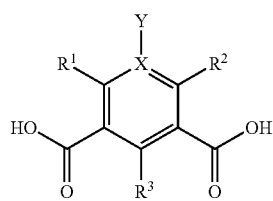

(I)

wherein X represents a carbon atom or nitrogen atom, Y represents a hydrogen atom, optionally substituted alkyl group having 1 to 4 carbon atoms, alkenyl group having 2 to 4 carbon atoms, alkoxy group having 1 to 4 carbon atoms, formyl group, acyloxy group having 2 to 4 carbon atoms, hydroxyl group, alkoxycarbonyl group having 2 to 4 carbon atoms, nitro group, cyano group, amino group, monoalkylamino group having 1 to 4 carbon atoms, dialkylamino group having 2 to 4 carbon atoms, acylamino group having 2 to 4 carbon atoms, sulfo group, sulfonate group or halogen atom in the case X represents a carbon atom, or Y is not present in the case X represents a nitrogen atom, and $R^1$, $R^2$ and $R^3$ respectively and independently represent a hydrogen atom, optionally substituted alkyl group having 1 to 4 carbon atoms or halogen atom.

X in general formula (I) is a carbon atom or nitrogen atom. Y is not present in the case X is a nitrogen atom.

In the case X is a carbon atom, Y is a hydrogen atom, optionally substituted alkyl group having 1 to 4 carbon atoms, alkenyl group having 2 to 4 carbon atoms, alkoxy group having 1 to 4 carbon atoms, formyl group, acyloxy group having 2 to 4 carbon atoms, hydroxyl group, alkoxycarbonyl group having 2 to 4 carbon atoms, nitro group, cyano group, amino group, monoalkylamino group having 1 to 4 carbon atoms, dialkylamino group having 2 to 4 carbon atoms, acylamino group having 2 to 4 carbon atoms, sulfo ($—SO_3H$) group, sulfonate group (such as $—SO_3Na$) or halogen atom.

Examples of alkyl groups having 1 to 4 carbon atoms include linear or branched alkyl groups, such as a methyl group, ethyl group, n-propyl group, isopropyl group, n-butyl group, isobutyl group or tert-butyl group.

Examples of optional substituents of the alkyl groups include alkoxy groups (such as a methoxy group, ethoxy group, n-propoxy group, isopropoxy group, n-butoxy group, isobutoxy group or tert-butoxy group), amino groups, monoalkylamino groups (such as a methylamino group), dialkylamino groups (such as a dimethylamino group), formyl group, epoxy groups, acyloxy groups (such as an acetoxy group, n-propanoyloxy group, n-butanoyloxy group, pivaloyloxy group or benzoyloxy group), alkoxycarbonyl groups (such as a methoxycarbonyl group, ethoxycarbonyl group or n-butoxycarbonyl group), and carboxylic anhydride groups (such as a $—CO—O—CO—R$ group, wherein R represents an alkyl group having 1 to 4 carbon atoms). In the case an alkyl group has a substituent, the number of substituents is preferably 1 to 3 and more preferably 1.

Examples of alkenyl groups having 2 to 4 carbon atoms include a vinyl group, allyl group, 1-propenyl group and butenyl group.

Examples of alkoxy groups having 1 to 4 carbon atoms include a methoxy group, ethoxy group, n-propoxy group, isopropoxy group, n-butoxy group, isobutoxy group and tert-butoxy group.

Examples of acyloxy groups having 2 to 4 carbon atoms include an acetoxy group, n-propanoyloxy group, n-butanoyloxy group, pivaloyloxy group and benzoyloxy group.

Examples of alkoxycarbonyl groups having 2 to 4 carbon atoms include a methoxycarbonyl group, ethoxycarbonyl group and n-butoxycarbonyl group.

Examples of monoalkylamino groups having 1 to 4 carbon atoms include a methylamino group. Examples of dialkylamino groups having 2 to 4 carbon atoms include a dimethylamino group. Examples of acylamino groups having 2 to 4 carbon atoms include an acetylamino group.

Examples of halogen atoms include fluorine, chlorine, bromine and iodine.

Examples of sulfonate groups include a lithium sulfonate group, sodium sulfonate group and potassium sulfonate group.

$R^1$, $R^2$ and $R^3$ in general formula (I) respectively and independently represent a hydrogen atom, optionally substituted alkyl group having 1 to 4 carbon atoms or halogen atom. $R^1$, $R^2$ and $R^3$ may be the same or different.

Examples of alkyl groups having 1 to 4 carbon atoms represented by $R^1$, $R^2$ and $R^3$ include linear or branched alkyl groups, such as a methyl group, ethyl group, n-propyl group, isopropyl group, n-butyl group, isobutyl group or tert-butyl group.

Examples of optional substituents of the alkyl groups include alkoxy groups (such as a methoxy group, ethoxy group, n-propoxy group, isopropoxy group, n-butoxy group, isobutoxy group or tert-butoxy group), amino groups, monoalkylamino groups (such as a methylamino group), dialkylamino groups (such as a dimethylamino group), formyl group, epoxy groups, acyloxy groups (such as an acetoxy group, n-propanoyloxy group, n-butanoyloxy group, pivaloyloxy group or benzoyloxy group), alkoxycarbonyl groups (such as a methoxycarbonyl group, ethoxycarbonyl group or n-butoxycarbonyl group), and carboxylic anhydride groups (such as a $—CO—O—CO—R$ group, wherein R represents an alkyl group having 1 to 4 carbon atoms). In the case an alkyl group has a substituent, the number of substituents is preferably 1 to 3 and more preferably 1.

Examples of halogen atoms include fluorine, chlorine, bromine and iodine.

In the case X is a nitrogen atom, an example of the dicarboxylic acid compound (I) is 3,5-pyridinedicarboxylic acid.

From the viewpoint of the ease of adopting a pseudo-diamondoid structure, it is preferable that $R^1$, $R^2$ and $R^3$ respectively and independently represent a hydrogen atom, alkyl group having 1 to 4 carbon atoms or halogen atom. In the case X is a carbon atom, Y is preferably a hydrogen atom, optionally substituted alkyl group having 1 to 4 carbon atoms, alkoxy group having 1 to 4 carbon atoms, nitro group or sulfonate group. The optionally substituted alkyl group having 1 to 4 carbon atoms is preferably a methyl group or tert-butyl group. The alkoxy group having 1 to 4 carbon atoms is preferably a methoxy group.

The dicarboxylic acid compound (I) is preferably a dicarboxylic acid in which $R^1$, $R^2$ and $R^3$ are hydrogen atoms, X is a carbon atoms, and Y is any of a hydrogen atom, methyl group, tert-butyl group, methoxy group, nitro group or sulfonate group. More specifically, isophthalic acid, 5-methylisophthalic acid, 5-tert-butylisophthalic acid, 5-methoxyisophthalic acid, 5-nitroisophthalic acid, sodium 5-sulfoisophthalate and lithium 5-sulfoisophthalate are preferable, isophthalic acid, 5-methylisophthalic acid and 5-nitroisophthalic acid are more preferable, and from the viewpoint of the separating material, 5-nitroisophthalic acid is most preferable. Two or more types of isophthalic acid may be used.

<Metal Ion>

The metal ion that composes the metal complex used in the separating material of the present invention is an ion of at least one type of metal selected from the group consisting of beryllium, magnesium, calcium, strontium, barium, titanium, vanadium, chromium, manganese, iron, ruthenium, cobalt, rhodium, nickel, palladium, platinum, copper, zinc and cadmium. Among these, a cobalt ion, nickel ion and zinc ion are preferable from the viewpoint of complex formation, and a zinc ion is more preferable.

A salt, hydroxide or oxide of the aforementioned metals can be used as a metal raw material when producing the metal complex of the present invention. Although a single metal raw material is preferably used for the metal raw material, two or more types of metal raw materials may also be used after mixing. Examples of these metal salts that can be used include organic acid salts, such as acetates or formates, and inorganic acid salts, such as hydrochlorides, hydrobromides, sulfates, nitrates or carbonates. Among these, hydroxides and oxides are preferable from the viewpoint of the formation of by-products accompanying the reaction, and oxides are more preferable.

<Dipyridyl Compound (II)>

The dipyridyl compound (II) used in the present invention is an organic ligand capable of bidentate coordination with a metal ion, and is represented by the following general formula (II):

L-Z-L  (II)

wherein L is represented by any of the following formulas:

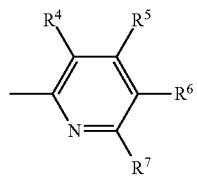

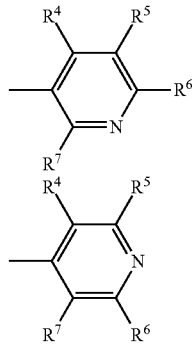

wherein $R^4$, $R^5$, $R^6$ and $R^7$ respectively and independently represent a hydrogen atom, alkyl group having 1 to 4 carbon atoms or a halogen atom, and Z represents —$CR^8R^9$—$CR^{10}R^{11}$— (wherein $R^8$, $R^9$, $R^{10}$ and $R^{11}$ respectively and independently represent a hydrogen atom, alkyl group having 1 to 4 carbon atoms, hydroxyl group or halogen atom), an alkylene group having 3 to 4 carbon atoms, —CH=CH—, —C≡C—, —S—S—, —N=N—, —O—$CH_2$—, —NH—$CH_2$— or —NHCO—).

$R^4$, $R^5$, $R^6$ and $R^7$ that compose L respectively and independently represent a hydrogen atom, alkyl group having 1 to 4 carbon atoms or halogen atom. Examples of alkyl groups having 1 to 4 carbon atoms and halogen atoms are as explained with respect to the dicarboxylic acid compound (I). $R^4$, $R^5$, $R^6$ and $R^7$ are preferably hydrogen atoms or alkyl groups having 1 to 4 carbon atoms in terms of the amount of gas adsorbed, and $R^4$, $R^5$, $R^6$ and $R^7$ are more preferably all hydrogen atoms.

Z represents —$CR^8R^9$—$CR^{10}R^{11}$— (wherein $R^8$, $R^9$, $R^{10}$ and $R^{11}$ respectively and independently represent a hydrogen atom, alkyl group having 1 to 4 carbon atoms, hydroxyl group or halogen atom), an alkylene group having 3 to 4 carbon atoms, —CH=CH—, —C≡C—, —S—S—, —N=N—, —O—$CH_2$—, —NH—$CH_2$— or —NHCO—. Examples of alkyl groups having 1 to 4 carbon atoms and halogen atoms are as explained with respect to the dicarboxylic acid compound (I). Examples of alkylene groups having 3 to 4 carbon atoms include a 1,3-propylene group, 1,4-butylene group and 2-methyl-1,3-propylene group.

From the viewpoint of easily adopting a pseudo-diamondoid structure, Z is preferably —$CR^8R^9$—$CR^{10}R^{11}$— (wherein $R^8$, $R^9$, $R^{10}$ and $R^{11}$ respectively and independently represent a hydrogen atom, alkyl group having 1 to 4 carbon atoms, hydroxyl group or halogen atom), an alkylene group having 3 to 4 carbon atoms, —CH=CH—, —S—S— or —NHCO—. In particular, Z is more preferably —$CR^8R^9$—$CR^{10}R^{11}$— (wherein $R^8$, $R^9$, $R^{10}$ and $R^{11}$ are all hydrogen atoms), —$CR^8R^9$—$CR^{10}R^{11}$— (wherein $R^8$ and $R^{10}$ are hydrogen atoms and $R^9$ and $R^{11}$ are hydroxyl groups), a 1,3-propylene group, —CH=CH—, —S—S— or —NHCO—.

From the viewpoint of easily adopting a pseudo-diamondoid structure, the dipyridyl compound (II) is preferably 1,2-di(4-pyridyl)ethylene, 1,2-di(4-pyridyl)ethane, 1,2-di(4-pyridyl)ethylene glycol, 1,3-di(4-pyridyl)propane, 4,4'-dipyridyl disulfide or N-(4-pyridyl)isonicotinamide.

The present invention is characterized by combining two or more types of the dipyridyl compound (II) to compose a metal complex. As a result of combining two or more types of the dipyridyl compound (II), there is the effect of increasing the recovery efficiency of 1,3-butadiene since the gate-opening pressure of 1,3-butadiene is lower in comparison with a metal complex composed from only one type of the dipyridyl compound (II).

Preferable combinations of the dipyridyl compound (II) include 1,2-di(4-pyridyl)ethylene and 1,2-di(4-pyridyl)ethane, 1,2-di(4-pyridyl)ethylene and 1,2-di(4-pyridyl)ethylene glycol, 1,2-di(4-pyridyl)ethylene and 4,4'-dipyridyl sulfide, 1,2-di(4-pyridyl)ethylene and N-(4-pyridyl)isonicotinamide, and 1,2-di(4-pyridyl)ethylene and 1,3-di(4-pyridyl) propane. Moreover, from the viewpoint of adsorption performance, the combinations of 1,2-di(4-pyridyl)ethylene and 1,2-di(4-pyridyl)ethane, 1,2-di(4-pyridyl)ethylene and 1,2-di(4-pyridyl)ethylene glycol, 1,2-di(4-pyridyl)ethylene and 4,4'-dipyridyl sulfide, and 1,2-di(4-pyridyl)ethylene and 1,3-di(4-pyridyl)propane are more preferable. The combination of 1,2-di(4-pyridyl)ethylene and 1,2-di(4-pyridyl) ethane is even more preferable.

The ratio between 1,2-di(4-pyridyl)ethylene and 1,2-di(4-pyridyl)ethane is such that the ratio of 1,2-di(4-pyridyl) ethane to the total amount (number of moles) of the dipyridyl compound (II) is preferably 5 mol % to 90 mol %. The ratio is more preferably 40 mol % to 80 mol %.

The ratio between 1,2-di(4-pyridyl)ethylene and 1,2-di(4-pyridyl)ethylene glycol is such that the ratio of 1,2-di(4-pyridyl)ethylene glycol to the total amount (number of moles) of the dipyridyl compound (II) is preferably 5 mol % to 40 mol %. The ratio is more preferably 10 mol % to 30 mol %.

The ratio between 1,2-di(4-pyridyl)ethylene and 4,4'-dipyridyl sulfide is such that the ratio of 4,4'-dipyridyl sulfide to the total amount (number of moles) of the dipyridyl compound (II) is preferably 5 mol % to 40 mol %. From the viewpoint of adsorption performance, the ratio is more preferably 10 mol % to 30 mol %.

The ratio between 1,2-di(4-pyridyl)ethylene and 1,3-di(4-pyridyl)propane is such that the ratio of 1,3-di(4-pyridyl) propane to the total amount (number of moles) of the dipyridyl compound (II) is preferably 5 mol % to 40 mol %. From the viewpoint of adsorption performance, the ratio is more preferably 10 mol % to 30 mol %.

<Metal Complex Production Method>

The metal complex of the present invention can be produced by reacting the dicarboxylic acid compound (I), a salt of at least one type of metal selected from the group consisting of beryllium, magnesium, calcium, strontium, barium, titanium, vanadium, chromium, manganese, iron, ruthenium, cobalt, rhodium, nickel, palladium, platinum, copper, zinc and cadmium, and two or more types of a dipyridyl compound capable of bidentate coordination with the metal ion for several minutes to several days in a solvent at normal pressure, and precipitating crystals. For example, the metal complex of the present invention can be obtained by mixing and reacting an aqueous solution or water-containing organic solvent solution of the aforementioned metal salt and an organic solvent solution containing the dicarboxylic acid compound (I) and two or more types of the dipyridyl compound (II) at normal pressure.

One example of the production method is a method that uses a wet grinder. The dicarboxylic acid compound (I), metal salt, two or more types of the dipyridyl compound (II), solvent and grinding balls are placed in the apparatus followed by carrying out the reaction while carrying out a grinding procedure.

In the aforementioned reaction, it is preferable that the raw materials be reacted in the wet grinder and the reaction be completed while grinding the reaction product in the form of the metal complex that precipitates in the form of crystals.

Examples of apparatuses used for wet grinding include pulverizers, such as a ball mill or rod mill, and mixers, such as a kneader. The use of a grinder is advantageous from the viewpoint of adsorption rate since a metal complex having a smaller particle diameter can be obtained in comparison with conventional hydrothermal synthesis methods and the like. In addition, production time can be shortened considerably since synthesis is completed in roughly several minutes to several hours.

The mixing ratio between the dicarboxylic acid compound (I) and the dipyridyl compound (II) when producing the metal complex is such that the ratio of the dicarboxylic acid compound (I) to the dipyridyl compound (II) is preferably within the range of a molar ratio of 1:5 to 8:1 and more preferably within the range of a molar ratio of 1:3 to 6:1. Although the target metal complex can be obtained even if the reaction is carried out outside these ranges, yield decreases and side reactions increase, thereby making this undesirable. The aforementioned ratio of the dipyridyl compound (II) is that based on the total amount of two or more types of the dipyridyl compound (II), and this applies similarly hereinafter.

The mixing ratio between the metal salt and dipyridyl compound (II) when producing the metal complex is such that the ratio of the metal salt to the dipyridyl compound (II) is preferably within the range of a molar ratio of 3:1 to 1:3 and more preferably within the range of a molar ratio of 2:1 to 1:2. In the case of a ratio outside these ranges, yield of the metal complex decreases and unreacted raw materials remain, thereby making it difficult to purify the resulting metal complex.

The molar concentration of the dicarboxylic acid compound (I) in a solution for producing the metal complex is preferably 0.005 mol/L to 5.0 mol/L and more preferably 0.01 mol/L to 2.0 mol/L. Although the target metal complex is obtained even if the reaction is carried out at a lower concentration than those indicated above, yield decreases, thereby making this undesirable. In addition, at a higher concentration than those indicated above, solubility decreases and the reaction may not proceed smoothly.

The molar concentration of the metal salt in the solution for producing the metal complex is preferably 0.005 mol/L to 5.0 mol/L and more preferably 0.01 mol/L to 2.0 mol/L. Although the target metal complex is obtained even if the reaction is carried out at a lower concentration than those indicated above, yield decreases, thereby making this undesirable. In addition, at a higher concentration than those indicated above, unreacted metal salt remains, thereby making it difficult to purify the resulting metal complex.

The molar concentration of the dipyridyl compound (II) in the solution for producing the metal complex is preferably 0.001 mol/L to 5.0 mol/L and more preferably 0.005 mol/L to 2.0 mol/L. Although the target metal complex is obtained even at a concentration lower than those indicated above, yield decreases, thereby making this undesirable. In addition, at a higher concentration than those indicated above, solubility decreases and the reaction may not proceed smoothly.

An organic solvent, water or a mixed solvent thereof can be used for the solvent used to produce the metal complex. Specific examples of solvents that can be used include methanol, ethanol, propanol, diethyl ether, dimethoxyethane, tetrahydrofuran, hexane, cyclohexane, heptane, benzene, toluene, methylene chloride, chloroform, acetone, ethyl acetate, acetonitrile, N,N-dimethylformamide, dimethylsulfoxide, water and mixed solvents thereof. A mixed solvent consisting of 1% by weight to 80% by weight of water and an organic solvent is preferable as a mixed solvent. An aprotic polar solvent, such as tetrahydrofuran, acetone, acetonitrile, N,N-dimethylformamide, N,N-diethylformamide or dimethylsulfoxide is preferable for the organic solvent used in a mixed solvent with water. Among these solvents, water alone or a mixed solvent of N,N-dimethylformamide and water is particularly preferable. The pH may be adjusted to a pH preferable for complex formation by adding an acid or base to the solvent.

The concentration of water in the mixed solvent is preferably 1% by weight to 80% by weight, more preferably 3% by weight to 60% by weight, and most preferably 5% by weight to 55% by weight from the viewpoint of the particle size of the metal complex formed.

The reaction temperature is preferably −20° C. to 150° C. and more preferably 50° C. to 130° C. The reaction time is preferably 1 hour to 24 hours and more preferably 2 hours to 10 hours. In the case of using a wet grinder, the reaction temperature may be 10° C. to 30° C. The reaction time can also be shortened to about 10 minutes to 2 hours.

Completion of the reaction can be confirmed by quantifying the residual amounts of raw materials by gas chromatography or high-performance liquid chromatography. Following completion of the reaction, the resulting mixed liquid is subjected to vacuum filtration to collect the precipitate followed by washing with an organic solvent and vacuum-drying for several hours at, for example, 60° C. to 100° C. to obtain the metal complex of the present invention. A highly crystalline metal complex has high purity and delivers superior adsorption performance. The pH may be adjusted to a suitable pH using an acid or base in order to enhance crystallinity.

<Structure of Metal Complex>

Figure 2:
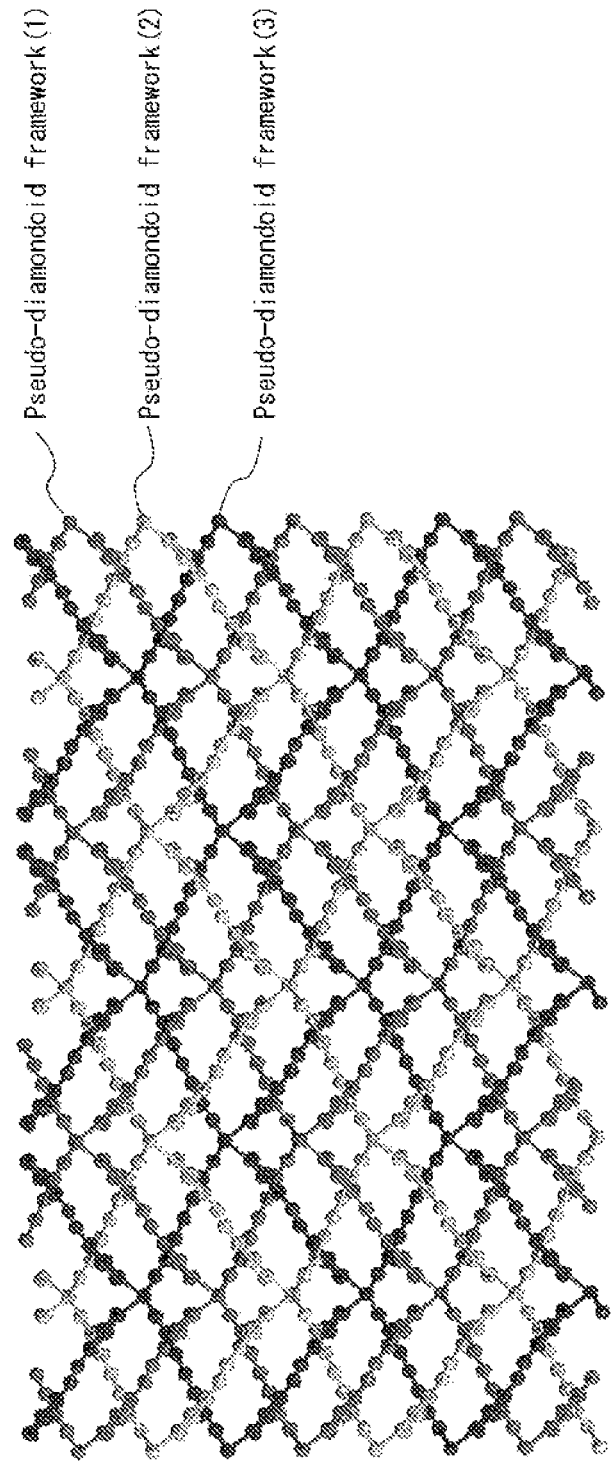
FIG. 2 is a schematic diagram showing the three-dimensional structure of a triply interpenetrating pseudo-diamondoid framework.

The metal complex of the present invention obtained in the manner described above has a three-dimensional structure that is a multiply interpenetrating pseudo-diamondoid framework formed by coordination of the carboxylate ions of two dicarboxylic acid compounds (I) and two dipyridyl compounds (II) per single metal ion. The structure of the pseudo-diamondoid framework is shown in FIG. 1, while a schematic diagram of the three-dimensional structure of a triply interpenetrating pseudo-diamondoid framework is shown in FIG. 2. The metal complex preferably has a structure that is a triply interpenetrating pseudo-diamondoid framework.

Although the metal complex according to the present invention is normally composed such that the ratio of the metal ion, dicarboxylic acid compound (I) and dipyridyl compound (II) is 1 mole:1 mole:1 mole, deviation from the aforementioned ratio is permitted provided the effects of the present invention are obtained.

In the present description, a "pseudo-diamondoid framework" is defined as a three-dimensional structure that resembles the structure of a diamond that is formed by coordination of carboxylate ions of two dicarboxylic acid compounds (I) and two dipyridyl compounds (II) per single metal ion.

In the present description, a "structure that is a multiply interpenetrating pseudo-diamondoid framework" is defined as a three-dimensional structure in which a plurality of pseudo-diamondoid frameworks is interpenetrating in a form that fills in their mutual pores. Whether or not the metal complex "has a structure that is a multiply interpenetrating pseudo-diamondoid framework" can be confirmed by, for example, crystal X-ray structural analysis or powder X-ray structural analysis.

The three-dimensional structure of the metal complex of the present invention can be changed even after synthesis. Pore structure and size also change accompanying a change in the three-dimensional structure of the metal complex. This structural change is presumed to depend on such factors as the type of adsorbate, pressure and temperature. Namely, it is believed that the metal complex of the present invention exhibits high selectivity since the degree of structural change varies depending on the adsorbates in addition to a difference in interaction between the pore surfaces and the adsorbate (the intensity of that interaction is proportional to the magnitude of the Lennard-Jones potential of the substance). Since the structure returns to its original structure after an adsorbate has been desorbed, pore structure would also return to its original structure.

In the present invention, gate-opening pressure can be controlled by modifying the intensity of the interaction among the interpenetrating pseudo-diamondoid frameworks using a dicarboxylic acid compound represented by general formula (I) and a dipyridyl compound represented by general formula (II). More specifically, by putting an organic ligand having greater steric hindrance (to be referred to as "dipyridyl compound B") than the organic ligand that composes the complex (to be referred to as "dipyridyl compound A") into a solid solution with the metal complex serving as the base (in the case of using one type of dipyridyl compound as an organic ligand capable of bidentate coordination), interaction among the pseudo-diamondoid frameworks weakens and the gate-opening pressure of the target adsorbate can be lowered. In this manner, the gate-opening pressure for a target adsorbate can be lowered, allowing only the target gas to be selectively adsorbed, by synthesizing using two or more types of dipyridyl compounds having different sizes.

The aforementioned adsorption mechanism is only presumptive. Even in the case the adsorption mechanism is not in accordance with that described above, it is encompassed in the scope of the present invention provided it satisfies the requirements provided for in the present invention.

<1,3-Butadiene Separation Method>

In the method of the present invention for separating 1,3-butadiene from a mixed gas containing 1,3-butadiene and hydrocarbons having four carbon atoms other than 1,3-butadiene, the mixed gas containing 1,3-butadiene as the separation target is contacted with the separating material of the present invention and the 1,3-butadiene is selectively adsorbed onto the separating material, after which the 1,3-butadiene adsorbed to the separating material is desorbed from the separating material and the released 1,3-butadiene is captured. The separating material is regenerated by desorption of the 1,3-butadiene.

Although there are no particular limitations on the hydrocarbon having four carbon atoms other than 1,3-butadiene contained in the mixed gas, the separating material of the present invention is particularly effective when separating 1,3-butadiene from a mixed gas containing as another gas a hydrocarbon having four carbon atoms, such as butenes including isobutene, 1-butene, trans-2-butene and cis-2-butene, or butanes including n-butane and isobutane, since it is difficult for conventional separating materials to separate these hydrocarbons from 1,3-butadiene due to the proximity of their boiling points to that of 1,3-butadiene.

Temperature and pressure conditions during contact between the mixed gas and separating material are preferably selected so that only the target 1,3-butadiene is effectively adsorbed onto the separating material.

The separation method comprises an adsorption step for contacting a mixed gas with the separating material of the present invention under conditions in which 1,3-butadiene is adsorbed onto the separating material. Conditions including adsorption pressure and adsorption temperature that enable the 1,3-butadiene to be adsorbed onto the separating material can be suitably determined depending on such factors as the apparatus design or required purity of the product gas. For example, the partial pressure of 1,3-butadiene in a mixed gas introduced into the adsorption step is preferably 10 kPa to 200 kPa and more preferably 30 kPa to 200 kPa. In addition, the adsorption temperature is preferably −5° C. to 100° C. and more preferably 0° C. to 50° C.

The separation method can be pressure swing adsorption or temperature swing adsorption.

In the case the separation method is pressure swing adsorption, the separation method comprises a step for contacting a mixed gas containing 1,3-butadiene with the separating material and making only the target 1,3-butadiene to be selectively adsorbed onto the separating material (adsorption step), followed by a step for reducing the pressure to a pressure that allows the 1,3-butadiene adsorbed to the separating material to be desorbed from the separating material (regeneration step). The desorption pressure can be suitably determined depending on such factors as the apparatus design or production efficiency. For example, the desorption pressure is preferably 0.05 kPa to 30 kPa and more preferably 0.05 kPa to 10 kPa.

Figure 3:
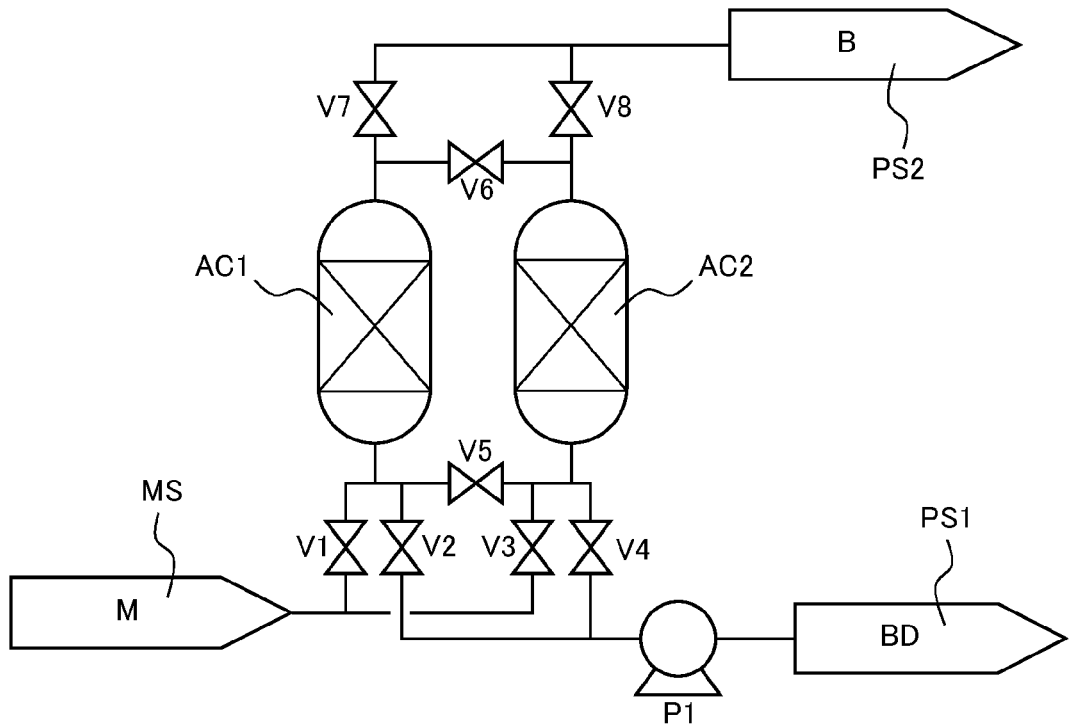
FIG. 3 is a schematic diagram of an apparatus for recovering 1,3-butadiene from a mixed gas by pressure swing adsorption.

The following provides a detailed explanation of pressure swing adsorption in the case the target gas is 1,3-butadiene with reference to FIG. 3. The separating material of the present invention is packed into adsorption column AC1 and adsorption column AC2. A mixed gas (M) containing 1,3-butadiene, butene, butane and the like is pressurized to about 0.3 MPa with a compressor and supplied from mixed gas storage tank MS to adsorption column AC1 packed with the separating material through valve V1 (to be abbreviated as "V1" and to apply similarly hereinafter). As can be understood from FIG. 7, if the partial pressure of 1,3-butadiene exceeds 40 kPa, the 1,3-butadiene is selectively adsorbed onto the separating material within adsorption column AC1 (adsorption step). On the other hand, butanes and butenes are not adsorbed and are discharged from adsorption column AC1. As a result, a concentrated butane/butene gas (B) is sent to product storage tank PS2 through V7. Next, adsorption column AC1 is aerated by vacuum pump P1 with V1, V5, V6 and V7 closed and V2 open. As can be understood from FIG. 7, when the pressure falls below 20 kPa, a gas (BD) consisting mainly of 1,3-butadiene adsorbed to the separating material in adsorption column AC1 is desorbed and sent to product storage tank PS1 (desorption step). An adsorption step is also similarly completed with respect to adsorption column AC2. After carrying out the desorption step of adsorption column AC1 for a prescribed period of time, V1, V2, V3, V4, V7 and V8 are closed and V5 and V6 are opened and a residual mixed gas in adsorption column AC2 is recovered into adsorption column AC1 by utilizing the pressure difference between adsorption column AC1 and adsorption column AC2 (pressure equalization step). Each product gas can be efficiently obtained without losing its purity by carrying out this pressure equalization step. Next, adsorption column AC2 is aerated by vacuum pump P1 with V2, V3, V5, V6 and V8 closed and V4 open, and a gas (BD) consisting mainly of 1,3-butadiene adsorbed at this time is desorbed and sent to product storage tank PS1. A mixed gas (M) containing 1,3-butadiene is supplied to adsorption column AC1 with V2, V3, V5, V6 and V8 closed and V1 and V7 open after which the adsorption step is carried out again. The adsorption and desorption operations in adsorption columns AC1 and AC2 are alternately repeated in a cycle suitably set with a timer and the like, resulting in continuous production of each product gas.

In the case the separation method is temperature swing adsorption, the separation method comprises a step for contacting a mixed gas containing 1,3-butadiene with the separating material and making only the target 1,3-butadiene to be selectively adsorbed onto the separating material (adsorption step), followed by a step for raising the temperature to a temperature that allows the 1,3-butadiene adsorbed to the separating material to be desorbed from the separating material (regeneration step). The desorption temperature can be suitably determined depending on such factors as the apparatus design or production efficiency. For example, the desorption temperature is preferably −5° C. to 150° C. and more preferably 20° C. to 100° C. The pressure is dependent on the range over which the temperature is allowed to swing, and a pressure from 0.1 MPa to the pressure at which the raw material gas liquefies is preferable.

In the case the separation method is pressure swing adsorption or temperature swing adsorption, the step for contacting the mixed gas with the separating material (adsorption step) and the step for changing the pressure or temperature to one at which 1,3-butadiene can be desorbed from the separating material (regeneration step) can be suitably repeated.

Membrane separation is another example of a separation method. A separation membrane can be obtained by disposing the metal complex on the surface of a porous support by crystal growth, for example. Examples of materials of the porous support that can be used preferably include alumina, silica, mullite, compositions composed of silica, alumina and other components, such as cordierite, porous sintered metals and porous glass. In addition, ceramics including other oxides, such as zirconia or magnesia, carbides or nitrides, such as silicon carbide or silicon nitride, gypsum, cement or mixtures thereof can also be used. The porosity of the porous support is typically about 30% to 80%, preferably 35% to 70% and most preferably 40% to 60%. In the case porosity is excessively low, the permeability of gases and other fluids decreases, thereby making this undesirable, while in the case porosity is excessively high, the strength of the support ends up decreasing, thereby making this undesirable. In addition, the pore size of the porous support is typically 10 nm to 10,000 nm and preferably 100 nm to 10,000 nm. A separation membrane having grown crystals of a metal complex on the surface of a porous support is obtained by immersing the porous support in a solution containing raw materials of the metal complex followed by heating as necessary.

In addition, a separation membrane can also be obtained by kneading the metal complex of the present invention with a polymeric material to disperse the metal complex in the polymeric material followed by forming into a film. Examples of polymeric materials include polymeric materials used for gas separation membranes, such as polyvinyl acetate, polyimide or polydimethylsiloxane.

In the case of membrane separation in which a mixed gas containing the target 1,3-butadiene is contacted with a separation membrane, the permeability P of each gas in the mixed gas is expressed as the product of the solubility S of each gas in the membrane and the diffusion coefficient D of each gas in the membrane. The higher the permeability P of a gas, the greater the selectivity at which the gas passes through the membrane. Therefore, such a gas can be separated and recovered from a mixed gas. Accordingly, by forming the metal complex of the present invention, which is highly selective for 1,3-butadiene, into a membrane, the obtained membrane allows 1,3-butadiene to selectively pass through. For example, when a mixed gas is passed through an inner tube of a double-walled tube provided with a gas-impermeable outer tube and the inner tube composed of a separation membrane, 1,3-butadiene selectively passes through the inner tube and is concentrated between the outer tube and the inner tube. Therefore, the target 1,3-butadiene can be separated.

Although the ratio of 1,3-butadiene in a mixed gas to be separated can be varied, this ratio is greatly dependent on the supply source of the mixed gas. In addition to 1,3-butadiene, a mixed gas may at least contain butenes, such as isobutene, 1-butene, trans-2-butene or cis-2-butene, and butanes, such as n-butane or isobutane as well as other hydrocarbons. The mixed gas preferably contains 10% by volume to 99% by volume of 1,3-butadiene based on the total volumetric ratio of 1,3-butadiene and other hydrocarbons (of which there may be multiple types) present in the mixed gas. The ratio of 1,3-butadiene is more preferably 20% by volume to 60% by volume.

The separating material of the present invention can be applied to separation of fractions having four hydrocarbons (C4 fractions) obtained by naphtha cracking. For example, after having pressurized a mixed gas containing about 40% by volume of 1,3-butadiene to 150 kPa or higher, the mixed gas is passed through an adsorption column packed with the separating material of the present invention for 1 minute to 10 minutes. Subsequently, after undergoing a pressure equalization step, the pressure is reduced to 20 kPa or lower with a vacuum pump, enabling the 1,3-butadiene adsorbed to the separating material to be recovered.

EXAMPLES

Although the following provides a detailed explanation of the present invention through examples thereof, the present invention is not limited to these examples. Analyses and evaluations in the following examples and comparative examples were carried out in the manner described below.
(1) Measurement of Adsorption-Desorption Isotherms Measurements were carried out by the volumetric method using a high-pressure gas adsorption apparatus. The samples were dried at 150° C. and 50 Pa for 6 hours prior to measurement to remove any adsorbed water and the like. Details of the analysis conditions are indicated below.
<Analysis Conditions>

Apparatus: BELSORP®-18HT manufactured by Bell Japan Inc. or BELSORP®-HP manufactured by Bell Japan Inc.

Equilibration pause time: 500 seconds
(2) Measurement of Powder X-Ray Diffraction Patterns X-ray diffraction patterns were measured according to a symmetrical reflection method at a scanning rate of 3°/minute over a diffraction angle range (2θ) of 3° to 50° using the MultiFlex X-ray diffraction system manufactured by Rigaku Corp. Mercury (ver. 2.3) available from the Cambridge Crystallographic Data Centre was used to convert single crystal structures to XRPD diffraction patterns.

Example 1

Synthesis of $[Zn(NO_2ip)(bpe)_{0.95}(bpa)_{0.5}]$

Zinc oxide (0.41 g, 5.0 mmol, 1 eq.), 5-nitroisophthalic acid (1.07 g, 5.0 mmol, 1.0 eq.), 1,2-di(4-pyridyl)ethane (0.05 g, 0.03 mmol, 0.05 eq.), 1,2-di(4-pyridyl)ethylene (0.87 g, 0.48 mmol, 0.95 eq.), distilled water (5 mL) and zirconia balls (diameter: 3 mm, 25 g) were added to a zirconia container (45 mL) followed by wet-grinding for 1 hour at room temperature (25° C.) and 400 rpm (using the Classic Line P-7 manufactured by Fritsch Japan Co., Ltd.). Subsequently, the contents were filtered using a Kiriyama® funnel, and the precipitated metal complex was washed with ion exchange water and ethanol in that order, followed by drying. 2.04 g (yield: 82%) of the metal complex were obtained in the form of a white solid. The resulting metal complex was confirmed to be a metal complex having a structure that is a triply interpenetrating pseudo-diamondoid framework as shown in FIGS. 1 and 2 by measurement of the powder X-ray diffraction pattern thereof. This was designated as "Metal Complex 1".

Examples 2 to 10 and Comparative Example 1

Metal Complexes 2 to 10 and Comparative Metal Complex 1 were produced in the same manner as Example 1 with the exception of changing the reaction raw materials to the substances and amounts shown in Table 1. Comparative Metal Complex 1 used only one type of the dipyridyl compound (II).

Comparative Example 2

Synthesis of $[Zn(NO_2ip)(bpe)]$

To a 500 mL recovery flask, 14.4 g (48.4 mmol) of zinc nitrate hexahydrate, 10.5 g (49.7 mmol) of 5-nitroisophthalic acid, 9.11 g (50.0 mmol) of 1,2-di(4-pyridyl)ethylene, 180 mL of DMF and 20 mL of distilled water were added. The resulting solution was heated and stirred for 6 hours at 120° C. After allowing to cool to room temperature, the precipitated solid was vacuum-filtered followed by washing with DMF, ion exchange water and ethanol in that order and vacuum-drying at 80° C. 23.3 g (yield: 97%) of Comparative Metal Complex 2 was obtained.

Comparative Example 3

Synthesis of $[Zn(NO_2ip)(bpa)]$

In a 100 mL hydrothermal reactor, 0.21 g (1.0 mmol) of 5-nitroisophthalic acid and 10 mL of an aqueous KOH solution (0.1 M) were placed. Moreover, 0.22 g (1.0 mmol) of zinc nitrate dihydrate, 0.19 g (1.0 mmol) of 1.2-di(4-pyridyl)ethane and 30 mL of distilled water were added. After heating for 72 hours at 160° C., the solution was cooled to room temperature at a cooling rate of 5° C./hour. The resulting white solid was filtered using a Kiriyama® funnel followed by washing with ion exchange water and ethanol in that order. As Comparative Example Complex 3, 0.40 g (yield: 88%) of the white solid were obtained.

Comparative Example 4

A typical zeolite adsorbent, Zeolite 13X (Union Showa K.K.), was used.

Comparative Example 5

A typical zeolite adsorbent, Zeolite NaY (Wako Pure Chemical Industries, Ltd.), was used.

<Adsorption Isotherms>

Figure 4:
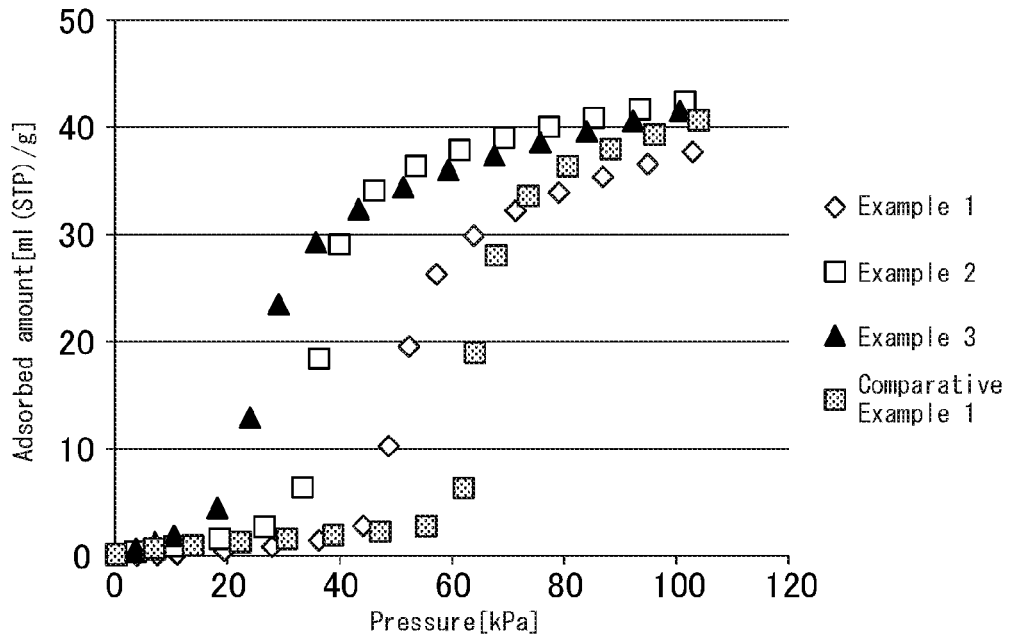
FIG. 4 is an adsorption isotherm of the metal complexes of Examples 1 to 3 and Comparative Example 1 with respect to 1,3-butadiene at 25° C.
Figure 5:
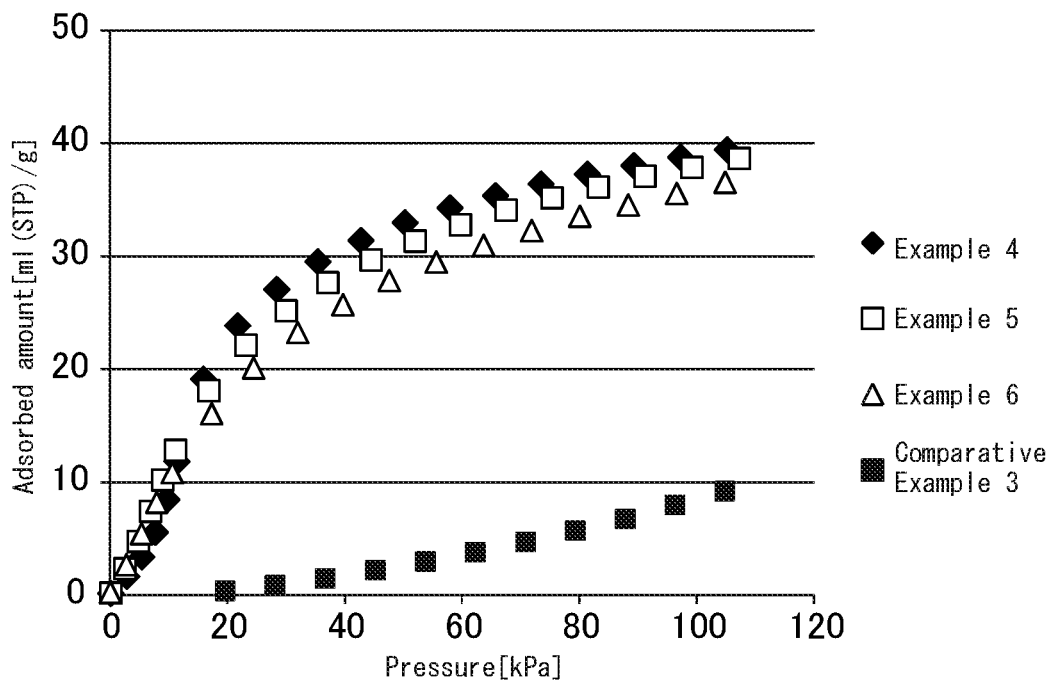
FIG. 5 is an adsorption isotherm of the metal complexes of Examples 4 to 6 and Comparative Example 3 with respect to 1,3-butadiene at 25° C.
Figure 6:
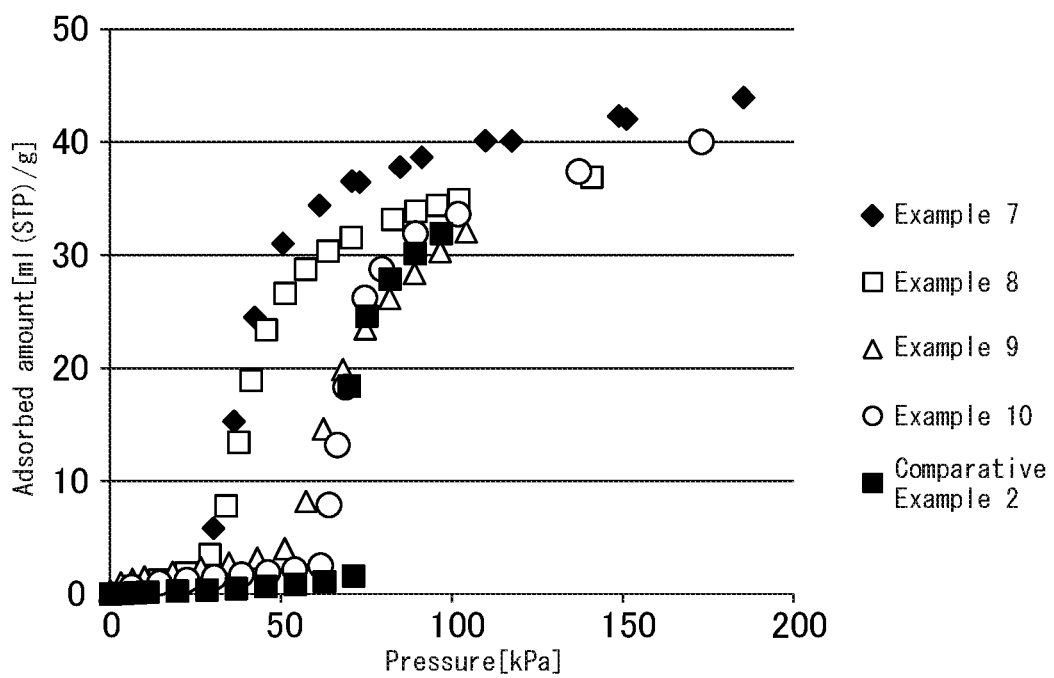
FIG. 6 is an adsorption isotherm of the metal complexes of Examples 7 to 10 and Comparative Example 2 with respect to 1,3-butadiene at 25° C.

The adsorption isotherms of 1,3-butadiene were measured at 25° C. for the metal complexes of Examples 1 to 10 and Comparative Examples 1 to 3. The results are shown in FIGS. 4 to 6. The metal complexes of Examples 1 to 10, which contained two types of dipyridyl compounds, began to adsorb 1,3-butadiene at a lower pressure than the complexes of Comparative Examples 1 to 3. Accordingly, the complex of the present invention is clearly superior as an adsorbent of 1,3-butadiene.

<Adsorption-Desorption Isotherms>

The adsorption-desorption isotherms of 1,3-butadiene, trans-2-butene and 1-butene at 25° C. were measured for Metal Complex 2 of Example 2 and the zeolite of Comparative Example 4. The results are shown in FIG. 7 and FIG. 8, respectively.

Figure 7:
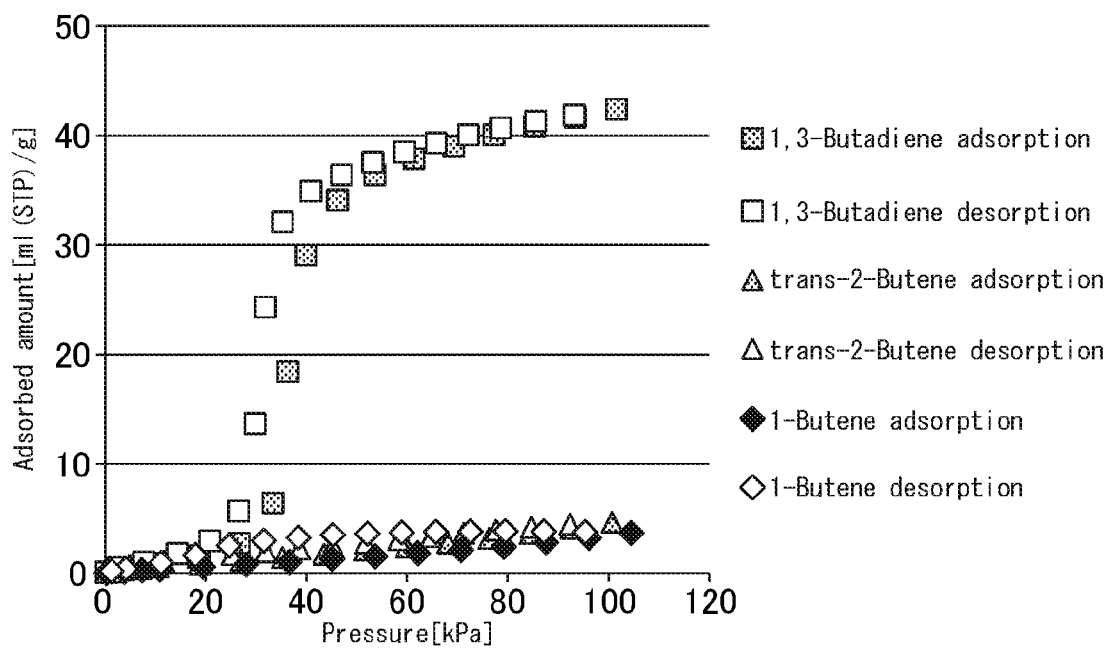
FIG. 7 is an adsorption-desorption isotherm of 1,3-butadiene, trans-2-butene and 1-butene in the metal complex of Example 2 at 25° C.
Figure 8:
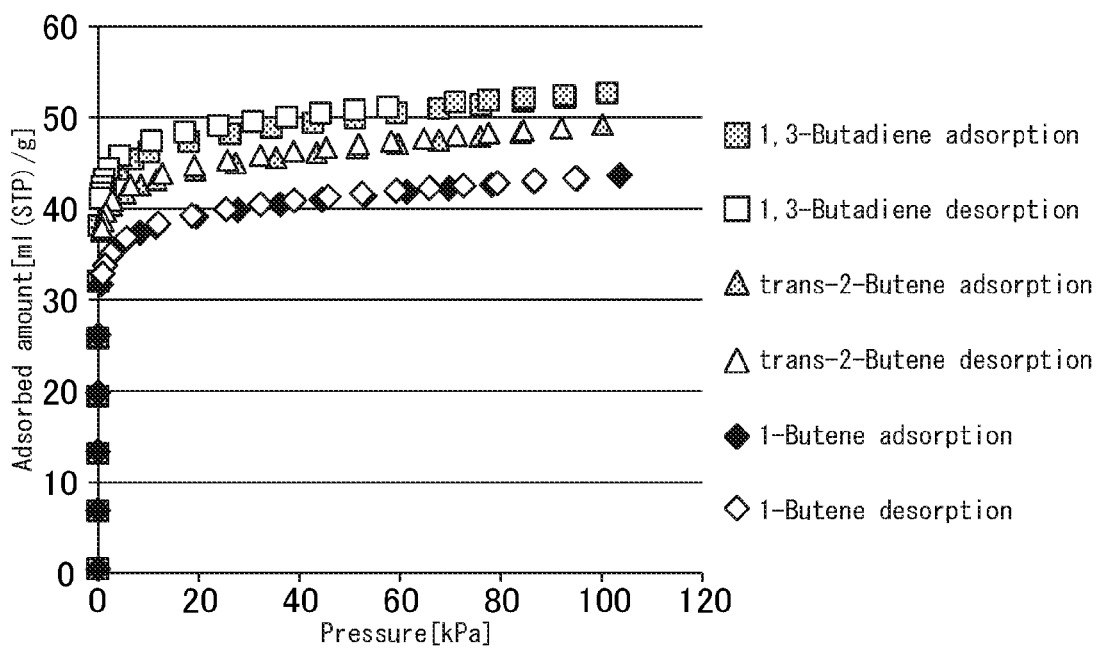
FIG. 8 is an adsorption-desorption isotherm of 1,3-butadiene, trans-2-butene and 1-butene in the separating material of Comparative Example 4 in the form of zeolite at 25° C.

FIG. 7 shows that Metal Complex 2 of the present invention selectively adsorbed 1,3-butadiene over a pressure range of 30 kPa to 100 kPa. Thus, when a mixed gas composed of 1,3-butadiene, trans-2-butene and 1-butene is contacted with Metal Complex 2 and the mixed gas is supplied at a partial pressure of 1,3-butadiene of 40 kPa or higher, only the 1,3-butadiene is adsorbed and concentrated. Next, since 1,3-butadiene desorbs when the supply of mixed gas is halted and the pressure is lowered to 20 kPa or lower, a concentrated gas of 1,3-butadiene can be obtained. On the other hand, with reference to FIG. 8, selective adsorption of 1,3-butadiene over a pressure range of 0 kPa to 110 kPa is inferior. Namely, not only 1,3-butadiene, but also trans-2-butene and 1-butene also end up being adsorbed and 1,3-butadiene cannot be sufficiently concentrated.

The adsorption-desorption isotherms of 1,3-butadiene, isobutene and isobutane at 25° C. were measured for Metal Complex 5 of Example 5 and the zeolite of Comparative Example 5. The results are shown in FIG. 9 and FIG. 10, respectively.

Figure 9:
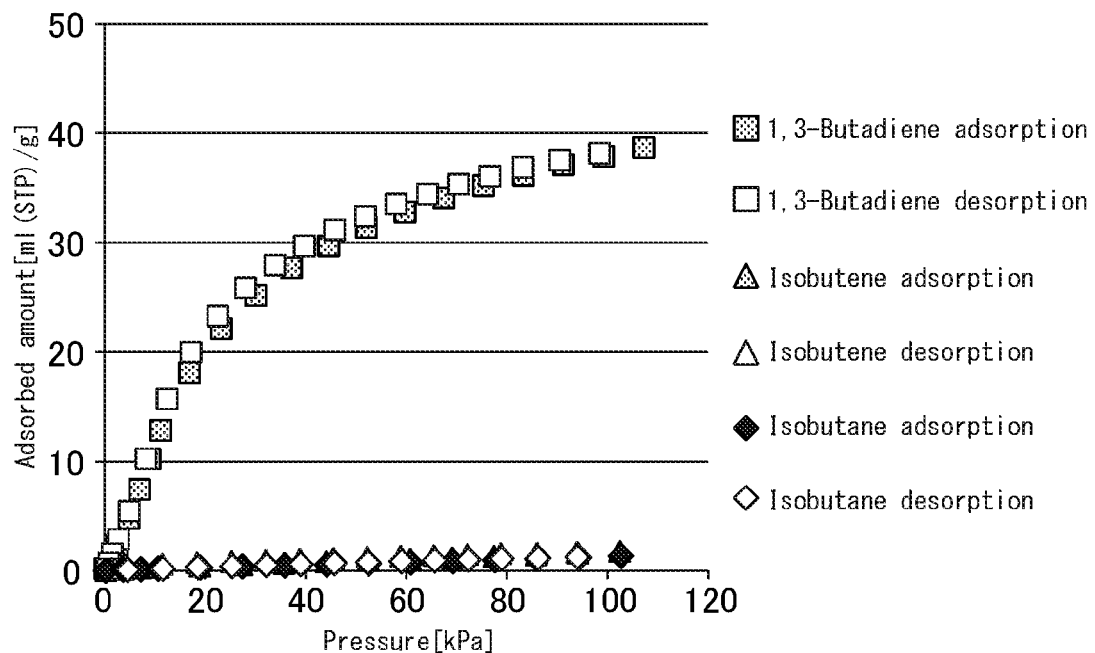
FIG. 9 is an adsorption-desorption isotherm of 1,3-butadiene, isobutene and isobutane in the metal complex of Example 5 at 25° C.
Figure 10:
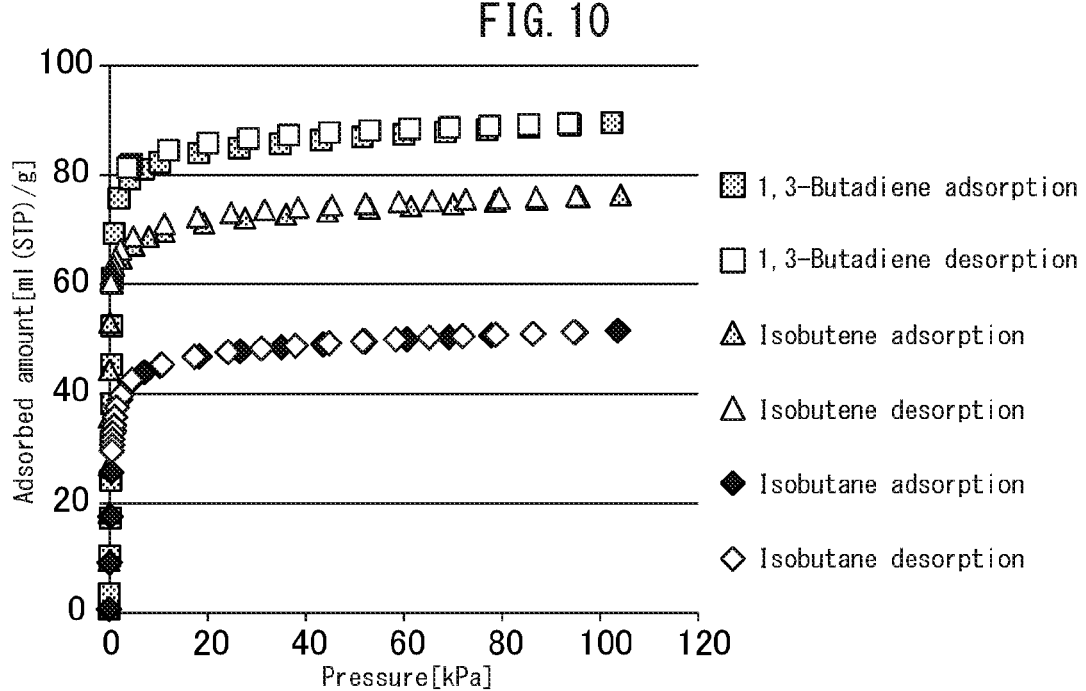
FIG. 10 is an adsorption-desorption isotherm of 1,3-butadiene, isobutene and isobutane in the separating material of Comparative Example 5 in the form of zeolite at 25° C.

According to FIG. 9, it is understood that Metal Complex 5 of the present invention selectively adsorbed 1,3-butadiene over a pressure range of 10 kPa to 100 kPa. Thus, when a mixed gas composed of 1,3-butadiene, isobutene and isobutane is contacted with Metal Complex 5 and the mixed gas is supplied at a partial pressure of 1,3-butadiene of 10 kPa or higher, only the 1,3-butadiene is selectively adsorbed and concentrated. Next, since 1,3-butadiene desorbs when the supply of mixed gas is halted and the pressure is lowered to 5 kPa or lower, a concentrated gas of 1,3-butadiene can be obtained. On the other hand, with reference to FIG. 10, selective adsorption of 1,3-butadiene over a pressure range of 0 kPa to 110 kPa is inferior. Namely, not only 1,3-butadiene, but also isobutene and isobutane also end up being adsorbed and 1,3-butadiene cannot be sufficiently concentrated.

<Mixed Gas Separation Experiment>

Metal Complex 5 (10.3 g) of Example 5 was packed into a stainless steel tube having a volume of 16 mL (inner diameter: 1 cm, length: 20 cm) followed by allowing a mixed gas composed of 1,3-butadiene, 1-butene and n-butane at a ratio (volumetric ratio) of 1:1:1 to pass through the tube at a spatial velocity (SV) of 3.8 per minute for 5 minutes at 25° C. and 0.15 MPa. Subsequently, the gas flow was halted and vacuuming was carried out over the course of 5 minutes using a diaphragm pump to recover the gas adsorbed to the complex (i.e. desorbed gas). After repeating this absorption-desorption procedure until a steady state was reached, analysis of the desorbed gas yielded a 1,3-butadiene concentration of 64% by volume. Based on this, the productivity of 1,3-butadiene per kilogram of separating material was calculated to be 46 L/hr. On the other hand, the zeolite (6.8 g) of Comparative Example 4 was packed into the aforementioned stainless steel tube, and after allowing a mixed gas composed of 1,3-butadiene, 1-butene and n-butane at a ratio (volumetric ratio) of 1:1:1 to pass through at a spatial velocity (SV) of 1.9 per minute at 25° C. and 0.15 MPa, the flow of gas was halted and vacuuming was carried out over the course of 30 minutes using a diaphragm pump to recover the gas adsorbed to the complex (i.e. desorbed gas). After repeating this absorption-desorption procedure until a steady state was reached, analysis of the desorbed gas yielded a 1,3-butadiene concentration of 41% by volume. Based on this, the productivity of 1,3-butadiene per kilogram of separating material was calculated to be 4.6 L/hr. On the basis thereof, the complex of the present invention is clearly superior as a separating material of 1,3-butadiene.

<Temperature Dependency>

The adsorption-desorption isotherms of 1,3-butadiene at 0° C. and 40° C. were measured for Metal Complex 4 of Example 4 and the zeolite of Comparative Example 4. The results are shown in FIG. 11 and FIG. 12, respectively.

Figure 11:
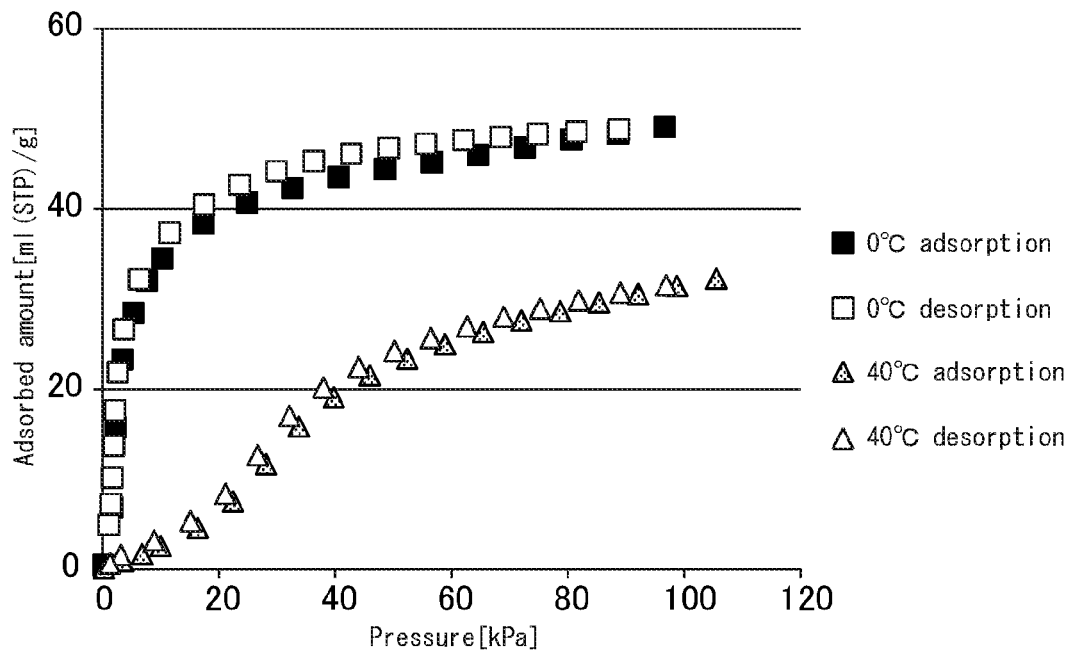
FIG. 11 is an adsorption-desorption isotherm of 1,3-butadiene in the metal complex of Example 4 at 0° C. and 40° C.
Figure 12:
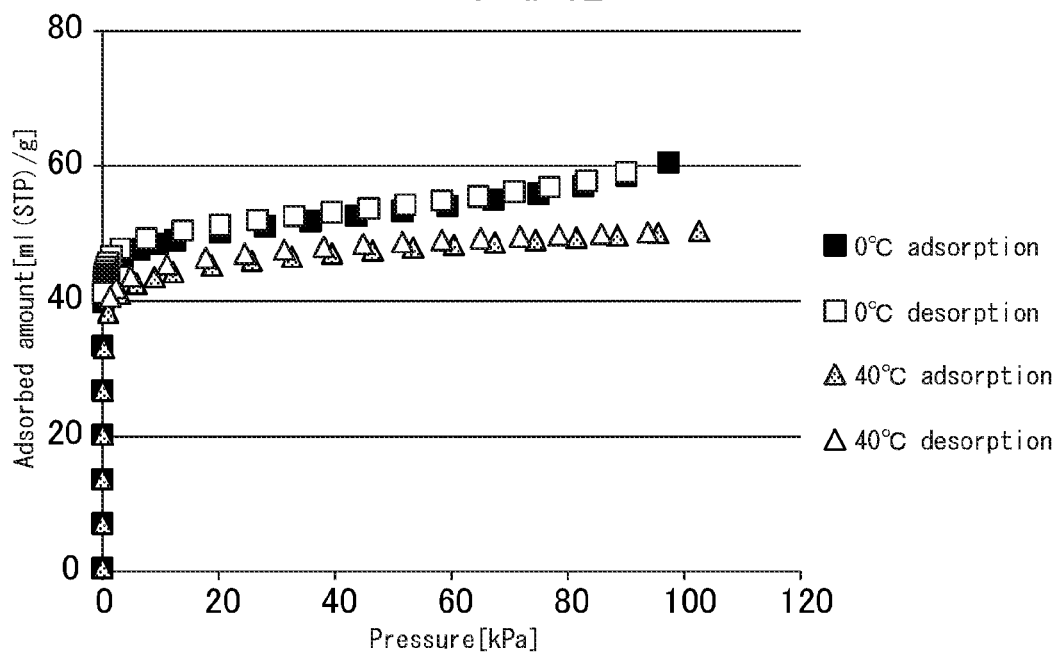
FIG. 12 is an adsorption-desorption isotherm of 1,3-butadiene in the separating material of Comparative Example 4 in the form of zeolite at 0° C. and 40° C.

According to FIG. 11, in the case of having raised the temperature from 0° C. to 40° C., the amount adsorbed to Metal Complex 4 of the present invention decreased considerably. Thus, when a mixed gas containing 1,3-butadiene is contacted with Metal Complex 4 at 0° C. and 1,3-butadiene is selectively absorbed thereto, followed by halting the flow of the mixed gas and raising the temperature of the system to 40° C., the 1,3-butadiene is desorbed and a concentrated 1,3-butadiene gas can be obtained. On the other hand, there were no differences in adsorbed amounts observed for the zeolite of FIG. 12 between temperatures of 0° C. and 40° C. Namely, since adsorbed 1,3-butadiene cannot be recovered even if the temperature of the system is raised, even if 1,3-butadiene is selectively adsorbed, it cannot be recovered. On the basis thereof, the complex of the present invention is clearly superior as a separating material of 1,3-butadiene.

TABLE 1

| | Metal Complex No. | Metal Raw Material (g) | Dicarboxylic Acid Compound (g) | Dipyridyl Compound A (g) | Dipyridyl Compound B (g) | B/(A + B) (mol %) | Yield (g) | Yield (%) |
|---|---|---|---|---|---|---|---|---|
| Example 1 | 1 | ZnO 0.40 | 5-NPA 1.07 | DP-ethylene 0.87 | DP-ethane 0.05 | 5 | 2.04 | 91 |
| Example 2 | 2 | ZnO 0.41 | 5-NPA 1.06 | DP-ethylene 0.82 | DP-ethane 0.10 | 10 | 1.98 | 87 |
| Example 3 | 3 | ZnO 0.41 | 5-NPA 1.06 | DP-ethylene 0.73 | DP-ethane 0.18 | 20 | 2.09 | 91 |
| Example 4 | 4 | ZnO 0.41 | 5-NPA 1.06 | DP-ethylene 0.55 | DP-ethane 0.37 | 40 | 1.99 | 88 |
| Example 5 | 5 | ZnO 0.41 | 5-NPA 1.06 | DP-ethylene 0.37 | DP-ethane 0.55 | 60 | 1.86 | 82 |
| Example 6 | 6 | ZnO 0.41 | 5-NPA 1.07 | DP-ethylene 0.19 | DP-ethane 0.74 | 80 | 2.02 | 89 |
| Example 7 | 7 | ZnO 0.41 | 5-NPA 1.05 | DP-ethylene 0.83 | DP-glycol 0.12 | 10 | 2.10 | 93 |
| Example 8 | 8 | ZnO 0.41 | 5-NPA 1.06 | DP-ethylene 0.73 | DP-glycol 0.22 | 20 | 2.00 | 88 |
| Example 9 | 9 | ZnO 0.41 | 5-NPA 1.07 | DP-ethylene 0.82 | DP-propane 0.11 | 10 | 2.07 | 91 |

TABLE 1-continued

| | Metal Complex No. | Metal Raw Material (g) | | Dicarboxylic Acid Compound (g) | | Dipyridyl Compound A (g) | | Dipyridyl Compound B (g) | | B/(A + B) (mol %) | Yield (g) | Yield (%) |
|---|---|---|---|---|---|---|---|---|---|---|---|---|
| Example 10 | 10 | ZnO | 0.41 | 5-NPA | 1.07 | DP-ethylene | 0.83 | DP-disulfide | 0.12 | 10 | 2.09 | 91 |
| Comp. Ex. 1 | Comp. 1 | ZnO | 0.41 | 5-NPA | 1.04 | DP-ethylene | 0.91 | None | — | 0 | 1.88 | 82 |
| Comp. Ex. 2 | Comp. 2 | Zn(NO$_3$)$_2$ | 14.4 | 5-NPA | 10.5 | DP-ethylene | 9.11 | None | — | 0 | 23.3 | 97 |
| Comp. Ex. 3 | Comp. 3 | ZnAc$_2$ | 0.22 | 5-NPA | 0.21 | None | — | DP-ethane | 0.19 | 100 | 0.40 | 88 |

5-NPA: 5-nitroisophthalic acid
DP-ethane: 1,2-di(4-pyridyl)ethane
DP-glycol: 1,2-di(4-pyridyl)ethylene glycol
DP-propane: 1,3-di(4-pyridyl)propane
DP-ethylene: 1,2-di(4-pyridyl)ethylene
DP-disulfide: 4,4'-dipyridyl disulfide

BRIEF DESCRIPTION OF REFERENCE SYMBOLS

MS: Mixed gas storage tank
PS1, PS2: Product storage tanks
AC1, AC2: Adsorption columns
P1: Vacuum pump
V1 to V8: Valves
M: Mixed gas
B: Concentrated butane/butene gas
BD: Gas consisting mainly of 1,3-butadiene

The invention claimed is:

1. A metal complex consisting of:
a dicarboxylic acid compound (I) represented by the following general formula (I):

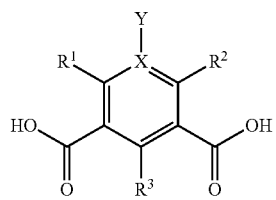

(I)

wherein X represents a carbon atom or nitrogen atom, Y represents a hydrogen atom, optionally substituted alkyl group having 1 to 4 carbon atoms, alkenyl group having 2 to 4 carbon atoms, alkoxy group having 1 to 4 carbon atoms, formyl group, acyloxy group having 2 to 4 carbon atoms, hydroxyl group, alkoxycarbonyl group having 2 to 4 carbon atoms, nitro group, cyano group, amino group, monoalkylamino group having 1 to 4 carbon atoms, dialkylamino group having 2 to 4 carbon atoms, acylamino group having 2 to 4 carbon atoms, sulfo group, sulfonate group or halogen atom in the case X represents a carbon atom or Y is not present in the case X represents a nitrogen atom, and $R^1$, $R^2$ and $R^3$ respectively and independently represent a hydrogen atom, optionally substituted alkyl group having 1 to 4 carbon atoms or halogen atom;

an ion of at least one type of metal selected from the group consisting of beryllium, magnesium, calcium, strontium, barium, titanium, vanadium, chromium, manganese, iron, ruthenium, cobalt, rhodium, nickel, palladium, platinum, copper, zinc and cadmium; and, a dipyridyl compound (II) represented by the following general formula (II):

L-Z-L            (II)

wherein L is represented by any of the following formulas:

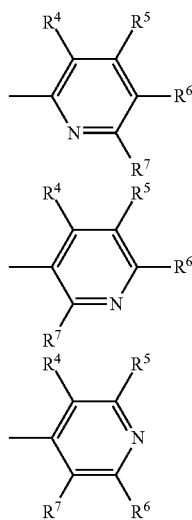

wherein $R^4$, $R^5$, $R^6$ and $R^7$ respectively and independently represent a hydrogen atom, alkyl group having 1 to 4 carbon atoms or a halogen atom, and Z represents —CR$^8$R$^9$—CR$^{10}$R$^{11}$— (wherein $R^8$, $R^9$, $R^{10}$ and $R^{11}$ respectively and independently represent a hydrogen atom, alkyl group having 1 to 4 carbon atoms, hydroxyl group or halogen atom), an alkylene group having 3 to 4 carbon atoms, —CH=CH—, —C≡C—, —S—S—, —N=N—, —O—CH$_2$—, —NH—CH$_2$— or —NHCO—);

wherein two or more different types of the dipyridyl compound (II) are contained as the dipyridyl compound (II), and only one type of the dicarboxylic acid compound (I) is contained as the dicarboxylic acid compound (I), and wherein the metal complex has a three-dimensional structure that is a multiply interpenetrating pseudo-diamondoid framework.

2. The metal complex according to claim 1, wherein Z in the general formula (II) is —CR$^8$R$^9$—CR$^{10}$R$^{11}$—(wherein $R^8$, $R^9$, $R^{10}$ and $R^{11}$ respectively and independently represent a hydrogen atom, alkyl group having 1 to 4 carbon atoms, hydroxyl group or halogen atom), an alkylene group having 3 to 4 carbon atoms, —CH=CH—, —S—S— or —NHCO—.

3. The metal complex according to claim 1, wherein a combination of the dipyridyl compound (II) is any of 1,2-di(4-pyridyl)ethylene and 1,2-di(4-pyridyl)ethane, 1,2-di(4-pyridyl)ethylene and 1,2-di(4-pyridyl)ethylene glycol, 1,2-di(4-pyridyl)ethylene and 4,4'-dipyridyl disulfide or 1,2-di(4-pyridyl)ethylene and 1,3-di(4-pyridyl)propane.

4. The metal complex according to claim 1, wherein the dicarboxylic acid compound (I) is one selected from the group consisting of isophthalic acid, 5-methylisophthalic acid and 5-nitroi sophthalic acid.

5. The metal complex according to claim 1, wherein the metal ion is at least one selected from the group consisting of a cobalt ion, nickel ion and zinc ion.

6. An adsorbent comprising the metal complex according to claim 1.

7. The adsorbent according to claim 6, wherein the adsorbent is an adsorbent for adsorbing carbon dioxide, hydrogen gas, carbon monoxide, oxygen gas, nitrogen gas, hydrocarbons having 1 to 5 carbon atoms, rare gas, hydrogen sulfide, ammonia, sulfur oxide, nitrogen oxide, siloxane, water vapor or organic vapor.

8. A separating material comprising the metal complex according to claim 1.

9. The separating material according to claim 8, wherein the separating material selectively separates 1,3-butadiene from a mixed gas containing 1,3-butadiene and a hydrocarbon having four carbon atoms other than 1,3-butadiene.

10. The separating material according to claim 9, wherein the hydrocarbon having four carbon atoms other than 1,3-butadiene is at least one selected from the group consisting of 1-butene, isobutene, trans-2-butene, cis-2-butene, isobutane and n-butane.

11. The separating material according to claim 8, wherein the separating material is a separating material for separating carbon dioxide, hydrogen gas, carbon monoxide, oxygen gas, nitrogen gas, hydrocarbons having 1 to 5 carbon atoms, rare gas, hydrogen sulfide, ammonia, sulfur oxide, nitrogen oxide, siloxane, water vapor or organic vapor.

12. A separation membrane comprising a porous support and the separating material according to claim 8 attached to the surface of the porous support.

13. A separation membrane comprising a polymeric material and the separating material according to claim 8 kneaded and dispersed in the polymeric material.

14. A method for producing the metal complex according to claim 1, comprising reacting a salt of at least one type of metal selected from the group consisting of beryllium, magnesium, calcium, strontium, barium, titanium, vanadium, chromium, manganese, iron, ruthenium, cobalt, rhodium, nickel, palladium, platinum, copper, zinc and cadmium, the dicarboxylic acid compound (I), and two or more types of the dipyridyl compound (II) and precipitating a metal complex, wherein wet grinding is carried out during the reaction.

15. A 1,3-butadiene separation method comprising: an adsorption step for contacting a separating material with a mixed gas containing 1,3-butadiene and a hydrocarbon having four carbon atoms other than 1,3-butadiene and selectively adsorbing 1,3-butadiene onto the separating material, followed by a regeneration step for desorbing the 1,3-butadiene adsorbed onto the separating material from the separating material and capturing the released 1,3-butadiene, wherein the separating material is the separating material according to claim 8.

16. The metal complex according to claim 2, wherein a combination of the dipyridyl compound (II) is any of 1,2-di(4-pyridyl)ethylene and 1,2-di(4-pyridyl)ethane, 1,2-di(4-pyridyl)ethylene and 1,2-di(4-pyridyl)ethylene glycol, 1,2-di(4-pyridyl)ethylene and 4,4'-dipyridyl disulfide or 1,2-di(4-pyridyl)ethylene and 1,3-di(4-pyridyl)propane.

* * * * *